United States Patent
Kalvins et al.

(10) Patent No.: US 9,908,893 B2
(45) Date of Patent: Mar. 6, 2018

(54) THIENO [2,3-B] PYRIDINES AS MULTIDRUG RESISTANCE MODULATORS

(71) Applicant: Latvian Institute of Organic Synthesis, Riga (LV)

(72) Inventors: Ivars Kalvins, Salaspils (LV); Aivars Krauze, Riga (LV); Signe Grinberga, Mezares (LV); Laura Krasnova, Riga (LV); Elina Jaschenko, Riga (LV); Ilona Domracheva, Riga (LV); Ilze Adlere, Saulkrasti (LV); Zigmars Andzans, Ogresgals (LV); Irina Shestakova, Riga (LV); Gunars Duburs, Riga (LV)

(73) Assignee: LATVIAN INSTITUTE OF ORGANIC SYNTHESIS, Riga (LV)

( * ) Notice: Subject to any disclaimer, the term of this patent is extended or adjusted under 35 U.S.C. 154(b) by 0 days.

(21) Appl. No.: 14/893,925

(22) PCT Filed: Jun. 11, 2013

(86) PCT No.: PCT/IB2013/054767
§ 371 (c)(1),
(2) Date: Nov. 24, 2015

(87) PCT Pub. No.: WO2014/199195
PCT Pub. Date: Dec. 18, 2014

(65) Prior Publication Data
US 2016/0137664 A1    May 19, 2016

(51) Int. Cl.
*C07D 495/04*    (2006.01)

(52) U.S. Cl.
CPC .................................. *C07D 495/04* (2013.01)

(58) Field of Classification Search
CPC .................................................. C07D 495/04
See application file for complete search history.

(56) References Cited

PUBLICATIONS

STN Chemical Database entry for RN 1136718-77-8 (3-amino-6-phenyl-4-(3,4,5-trimethoxyphenyl)thieno[2,3-b]pyridin-2-yl)(naphthalen-2-yl)methanone Entered STN: Apr 19, 2009.*
El-Louh "Synthesis of dihydropyridine, alkylthiopyridine, thienopyridine, and pyridothienopyrimidine derivatives." Asian Journal of Chemistry, 2007, 19(2), 1283-1292.*
Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2003, 74, 76-78.*

* cited by examiner

*Primary Examiner* — David K O'Dell
(74) *Attorney, Agent, or Firm* — Colin P. Abrahams

(57) ABSTRACT

The thieno[2,3-b]pyridines of general formula (I),

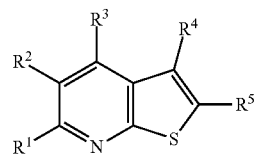

wherein
$R^1$ is Me, $C_6H_5$, 3,4,5-$(OMe)_3C_6H_2$, $NH_2$;
$R^2$ is H, CN, COMe, $COOC_{1-4}$alkyl, $COOC_2H_4OMe$, $COOC_2H_4OPr(n)$;
$R^3$ is $C_6H_4R^6$, 3,4-$OCH_2O$—$C_6H_3$; 2-furanyl;
  $R^6$ is 4-Cl, 4-$NO_2$, 4-$N(C_{1-4}alkyl)_2$, 3-$(C_{1-4}alkyloxy)$, 4-$(C_{1-4}alkyloxy)$, 3,4-$(C_{1-4}alkyloxy)_2$, 3,4,5-$(C_{1-4}alkyloxy)_3$;
$R^4$ is $NH_2$, NHCOMe;
$R^5$ is CN, COMe, $COC_6H_4R^7$; CO-(2-naphthyl);
  $R^7$ is H, 4-F, 4-Cl, 3-OMe, 4-OMe, 2,4-$(OMe)_2$, 3,4,5-$(OMe)_3$
as multidrug resistance modulators to increase the effectiveness of chemotherapy in cancer treatment.

4 Claims, No Drawings

THIENO [2,3-B] PYRIDINES AS MULTIDRUG RESISTANCE MODULATORS

FIELD OF THE INVENTION

This invention relates to novel thieno[2,3-b]pyridine derivatives and their use as multidrug resistance modulators to increase the effectiveness of chemotherapy in cancer treatment.

BACKGROUND OF THE INVENTION

Chemotherapy as cancer therapy has found clinical application in the treatment of almost every type of cancer. One of the major problems in cancer chemotherapy is the development of resistance to cytotoxic drugs. Patients who do not respond to a first course of chemotherapy relapse because tumor cells develop resistance against chemotherapeutic agents or has acquired resistance to cytotoxic agents used in a previous treatment. A tumor may also manifest resistance to a cytotoxic agent to which it has not been previously exposed. Multidrug resistance (MDR) in tumor cells has a significant impact on the efficacy of cancer chemotherapy and appears as a major obstacle in the modern cancer treatment. MDR is mainly related to the expression of the adenosine triphosphate ATP-binding cassette (ABC) transporters. P-glycoprotein (P-gp) (the best studied target for reverting MDR), multidrug resistance-associated protein (MRP1) and the breast cancer resistance protein (BCRP) as a major MDR proteins actively transport a wide variety of structurally different substrates out of the tumor cells, thereby decreasing their intracellular concentrations. Many actual chemotherapeutic agents are considered as potential P-gp, MRP1 and BCRP substrates (Szakács et al, Nat Rev Drug Discov 3: 219-34 (2006); Szakács et al., Drug Resistance in Cancer Cells 1-20 (2009)).

From all numerous efforts to overcome MDR like transcription control of P-gp expression the most promising approach has been the development of MDR modulators that are able to increase the intracellular drug levels in co-application with MDR substrates by the efflux pump inhibition. Substances of different groups have been used as P-gp inhibitors. $Ca^{2+}$ channel blocker verapamil is the most investigated and often used as reference compound, but unfortunately, in combination with actual anticancer drugs cardiotoxicity was observed (Pennock et al., J Natl Cancer Inst 83: 105-10 (1991)).

The functional unit of an ABC transporter contains two transmembrane domains (TMDs) and two nucleotide ATP-binding domains (NBDs). Transporters such as ABCG2 (BCRP) contain only one TMD and one NBD forms dimers.

Several ABC transporters have been found to be overexpressed in cancer cell lines under selective conditions. It was shown that the major mechanism of MDR in most cultured cancer cells involves P-gp, MRP1 and BCRP transport proteins. ABC transporters control not only the drug release to the cell, but also the intracellular compartmentalization or division between the cytoplasm and nucleus.

P-gp, a member of the ABCB subfamily, confers the strongest resistance to the wide variety of compounds. P-gp transports vinca alkaloids, anthracyclines, epipodophyllotoxins and taxanes. P-gp is normally expressed in epithelium of the liver, kidney and gastrointestinal tract at pharmacological barrier sites in stem cells and cells of immune system.

MRP1 is a member of ABCC subfamily and confers resistance to several hydrophobic compounds that are also P-gp substrates. However, MRP1 can export glutathione, glucuronate or sulphate conjugates of organic anions. MRP1 is expressed in wide range of tissues, tumors and cancer cell lines.

BCRP is a member of ABCG subfamily. The substrate specificity of BCRP overlaps considerably with that of P-gp. BCRP is involved in the mechanism of resistance to a topoisomerase I inhibitor (topotecan) or topoisomerase II inhibitor (mitoxantrone). BCRP does not act on paclitaxel or vincristine transport, which are excreted by P-gp, and BCRP is involved in excretion of a camptothecin derivative, which is barely transported by P-gp (Kruijtzer et al., J Clin Oncol 20: 2943-50 (2002)). BCRP is expressed in many normal tissues, including liver, placenta, brain, hematopoietic stem cells and other types of stem cells.

Besides the clinically important drugs, several fluorescent compounds are transported by P-gp, MRP1 and BCRP such as rhodamine 123 (P-gp), calcein (MRP1), Hoechst 33342 (P-gp, BCRP). These fluorescent compounds are used in studies of ABC transporters in cell lines.

Therefore, there is an actual need in MDR modulators, which are non-toxic, have weak influence (or no influence) on cardiovascular system and would effectively inhibit adenosine triphosphate binding cassette transport—modulate multidrug resistance in tumor cells and rise effectiveness of chemotherapy.

At the same time, thieno[2,3-b]pyridines are known to be biologically active substances, possessing, for example, PI3K inhibition activity, antiviral activity, osteogenesis promotion activity and modulating properties towards metabotropic glutamate receptors.

Thus, thieno[2,3-b]pyridines having phosphatidylinositide 3-kinases (PI3K) inhibitors activity have been disclosed in WO 2012/003262 A1.

Thieno[2,3-b]pyridines exhibiting nicotinamide adenine dinucleotide phosphate (NADPH) oxidase II inhibitor activity have been disclosed in WO 2011/075559 A1.

Thieno[2,3-b]pyridines proposed as inhibitors of human mitogen-activated protein kinase (MEK) enzymes are disclosed in WO 2009/153554 A1, WO 2009/013462 A1, WO 2009/093008 A1, WO 2007/088345 A1.

Thieno[2,3-b]pyridines possess antiviral activity, and more specifically are useful for treating HIV (Human Immunodeficiency Virus) infection (WO 2010/130842 A1, WO 2009/062288 A1) or Hepatitis C (US 2006/0019976 A1).

Thieno[2,3-b]pyridines have been reported to be useful for promoting osteogenesis, suppressing bone resorption and/or improving bone density; for prevention or treatment of osteopathy (for example, osteoporosis, in particular postmenopausal osteoporosis, senile osteoporosis or secondary osteoporosis caused by the use of steroids or immunosuppressants), osteopenia or bone destruction associated with rheumatoid arthritis, Paget's disease of bone, bone fracture or dysostosis due to dwarfism or osteoarthritis (EP 1764367 A1).

Thieno[2,3-b]pyridines have been claimed as potent modulators of metabotropic glutamate receptors (for mGluR5 and mGluR1 receptor subtype reported in WO 2007/072090 A1 and WO 2007/072091 A1, mGluR2 receptor subtype reported in WO 2006/030031 A1).

Thieno[2,3-b]pyridines have IκB kinase (IKK) complex inhibitor activity, therefore are useful in the treatment of IKK mediated diseases including autoimmune diseases, inflammatory diseases, cardiovascular disease and cancer have been disclosed in US 2007/0293533 A1.

Thieno[2,3-b]pyridines as inhibitors of tumor necrosis factor (TNF) have been disclosed in WO 2006/074919 A2.

Thieno[2,3-b]pyridines have been reported as vanilloid receptor 1 (VR1 or TRPV1) antagonists in WO 2006/068618 A1.

Thieno[2,3-b]pyridines are active on the $GABA_B$ receptor and can be used in treating CNS disorders (WO 2006/063732 A1).

Thieno[2,3-b]pyridines which modulate $K^+$ channel (possess inhibitor activity) have been described in WO 2006/061642 A1.

Thieno[2,3-b]pyridines that are selective allosteric modulators of the $M_4$ subtype of muscarinic receptors, useful for treatment of disorders associated with $M_4$ muscarinic receptors have been reported in WO 2006/047124 A1.

However, there are no reports of thieno[2,3-b]pyridines exhibiting multidrug resistance modulating properties.

DESCRIPTION OF THE INVENTION

We have unexpectedly discovered, that thieno[2,3-b]pyridines of general formula (I) are effective as MDR modulators:

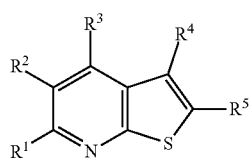

(I)

wherein
$R^1$ is $C_{1-4}$alkyl, $C_6H_5$, 3,4,5-$(OMe)_3C_6H_2$, $NH_2$;
$R^2$ is H, CN, COMe, $COOC_{1-4}$alkyl, $COOC_2H_4OC_{1-4}$alkyl;
$R^3$ is $C_6H_4R^6$, 3,4-$OCH_2O$—$C_6H_3$; 2-furanyl;
  $R^6$ is 4-Cl, 4-$NO_2$, 4-$N(C_{1-4}alkyl)_2$, 3-$(C_{1-4}$alkyloxy), 4-$(C_{1-4}$alkyloxy), 3,4-$(C_{1-4}$alkyloxy)$_2$, 3,4,5-$(C_{1-4}$alkyloxy)$_3$;
$R^4$ is $NH_2$, NHCOMe;
$R^5$ is CN, COMe, $COC_6H_4R^7$; CO-(2-naphthyl);
  $R^7$ is H, 4-F, 4-Cl, 3-OMe, 4-OMe, 2,4-$(OMe)_2$, 3,4,5-$(OMe)_3$ Thieno[2,3-b]pyridines of the formula (I) were synthesized by the following scheme.

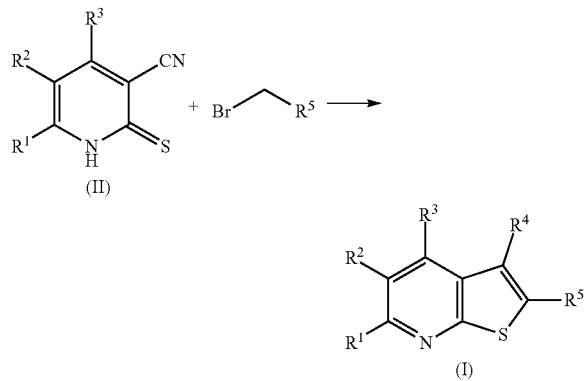

By treatment of 5-cyano-1,6-dihydro-6-thioxopyridines with carbo function containing alkylhalides in presence of base first alkylation takes place. The formed intermediates 2-alkylsulphanyl-3-cyanopyridines undergo Thorpe-Ziegler cyclization giving thieno[2,3-b]pyridines (compounds of formula (I)). Amino group in position 3 ($R^4=NH_2$) was acetylated to give compounds of the formula (I) ($R^4$=NHCOMe). A series of original 5-cyano-1,6-dihydro-6-thioxopyridines and α,β-unsaturated ketones as intermediates were synthesized.

Thieno[2,3-b]pyridines of the formula (I) were tested to reveal MDR-blocking activity. The potency of P-glycoprotein-mediated MDR modulator in vitro was evaluated in the drug sensitive human sarcoma MES-SA cells and doxorubicin (DOX) resistant cells by accumulation of fluorescent substrate—rhodamine 123. Effects on MRP1-mediated drug efflux were observed in the DOX resistant human lung carcinoma H69AR cells using calcein AM assay. BCRP1-mediated drug efflux was also evaluated using fluorescent substrate Hoechst 33342 in the mitoxantrone resistant human sarcoma MESSA/MX2 cells. The half-maximal effective concentrations ($EC_{50}$) were calculated from dose response curve as the most effective method to compare MDR-modulating activities of compounds of formula (I) with a reference compounds Verapamil, MK-571 and Glivec.

As $Ca^{2+}$ channel blocker Verapamil in combination with actual anticancer drugs have revealed cardio toxicity, influence of compounds of the formula (I) on cardiovascular system as well as their toxicity were tested. Changes in intracellular [$Ca^{2+}$] concentration were studied using A7R5 (rat aorta smooth muscle) cells and Fluo-4 NW Calcium Assay Kit ("Invitrogen", Sweden) according to manufacturer's instructions.

MDR modulating activity, intracellular $Ca^{2+}$ values and $LD_{50}$ values of tested compounds of the formula (I) are given in table 3.

2-COAr, 3-$NH_2$, 4-Ar, 5-COMe or 5-COOAlk and 6-Me groups are essential and together with thieno[2,3-b]pyridine scaffold determine MDR modulating activity. Exchange of COAr group in position 2 for COMe, CONHAr or CN groups, acylation of amino group in position 3, removing of acetyl or ester groups in position 5 (in case of 5-H and 5-CN substituents), as well as exchange of Me group in position 6 with aryl or amino groups lead to diminution of activity. The series bearing $R^1$=Me, $R^2$=COOAlk, $R^3$=3,4,5-$(OMe)_3C_6H_2$ and $R^4$=4-$MeOC_6H_4CO$ are the most potent MDR modulators exceeding significantly reference compounds Verapamil, MK-571 and Glivec. Activity is increased by changing of COMe group for COOMe, reaching maximum in case of COOEt and $COOC_2H_4OMe$ groups, but slightly reduced by introduction of more lipophilic $COOC_2H_4OC_3H_7$ and COOBu(n) groups in position 5.

Substitution of $R^3$=3,4,5-$(OMe)_3C_6H_2$ group in position 4 for 3,4-$(OMe)_2C_6H_3$, 3-$OMeC_6H_4$, 4-$OMeC_6H_4$, 4-$OMeC_6H_4$, 4-$OHC_6H_4$, 4-$ClC_6H_4$ groups, as well as substitution of $R^4$=4-$OMeC_6H_4CO$ group in position 2 for 2,4-$(OMe)_2C_6H_3CO$, 3-$OMeC_6H_4CO$, $C_6H_5CO$, 4-$ClC_6H_4CO$ and 4-$FC_6H_4CO$ groups lead to weakening of activity.

Thieno[2,3-b]pyridines bearing $R^1$=Me, $R^2$=COOAlk, $R^3$=3,4,5-$(OMe)_3C_6H_2$ and $R^4$=COAr (compounds OSI-9767, OSI-9995, OSI-10102, OSI-10103, OSI-10205, OSI-10206, OSI-10267) inhibit three MDR transport proteins: P-gp, MRP1 and BCRP1.

Thieno[2,3-b]pyridines bearing $R^1$=Me, $R^2$=COOAlk, $R^3$=4-$NMe_2C_6H_4$ or $(OMe)_nC_6H_{5-n}$, and $R^4$=$OMeC_6H_4CO$ groups (compounds OSI-10175, OSI-10214, OSI-10215, OSI-10240, OSI-10266, OSI-10276) selectively inhibit P-gp and BCRP1.

Thieno[2,3-b]pyridines with varied MDR-blocking activity (OSI-9767, OSI-9995, OSI-9998, OSI-9999, OSI-10102, OSI-10103, OSI-10125, OSI-10205, OSI-10206, OSI-10267, OSI-10302) exceeding significantly reference compounds Verapamil, MK-571, Reversan and Glivec, reveal more than ten times lower $Ca^{2+}$ antagonist effect than Verapamil (less cardiovascular side effects expected) and being non-toxic ($LD_{50}$>2000 mg/kg) are potential agents to overcome MDR problem in clinic.

According to the current invention, the most preferred thieno[2,3-b]pyridines (I) are those listed in the Table 1.

TABLE 1

Most preferred thieno[2,3-b]pyridines (I).

| Compound No. | Compound name | |
|---|---|---|
| 1 | OSI-10036 | 5-Acetyl-3-amino-4-(3,4-dimethoxyphenyl)-2-(4-methoxybenzoyl)-6-methyl-thieno[2,3-b]pyridine |
| 2 | OSI-10039 | 5-Acetyl-3-amino-2-(2,4-dimethoxybenzoyl)-4-(3,4-dimethoxyphenyl)-6-methyl-thieno[2,3-b]pyridine |
| 3 | OSI-10125 | 5-Acetyl-3-amino-2-(4-methoxybenzoyl)-6-methyl-4-(3,4,5-trimethoxyphenyl)-thieno[2,3-b]pyridine |
| 4 | OSI-10120 | 5-Acetyl-3-amino-2-(2,4-dimethoxybenzoyl)-6-methyl-4-(3,4,5-trimethoxyphenyl)-thieno[2,3-b]pyridine |
| 5 | OSI-10215 | 3-Amino-2-(4-methoxybenzoyl)-4-(4-methoxyphenyl)-6-methyl-thieno[2,3-b]-pyridine-5-carboxylic acid methyl ester |
| 6 | OSI-9998 | 3-Amino-4-(3,4-dimethoxyphenyl)-2-(4-methoxybenzoyl)-6-methyl-thieno[2,3-b]-pyridine-5-carboxylic acid methyl ester |
| 7 | OSI-10106 | 3-Amino-2-(2,4-dimethoxybenzoyl)-4-(3,4-dimethoxyphenyl)-6-methyl-thieno[2,3-b]pyridine-5-carboxylic acid methyl ester |
| 8 | OSI-10105 | 3-Amino-2-(4-fluorobenzoyl)-6-methyl-4-(3,4,5-trimethoxyphenyl)thieno[2,3-b]-pyridine-5-carboxylic acid methyl ester |
| 9 | OSI-10104 | 3-Amino-2-(4-chlorobenzoyl)-6-methyl-4-(3,4,5-trimethoxyphenyl)thieno[2,3-b]-pyridine-5-carboxylic acid methyl ester |
| 10 | OSI-10103 | 3-Amino-2-(4-methoxybenzoyl)-6-methyl-4-(3,4,5-trimethoxyphenyl)thieno[2,3-b]pyridine-5-carboxylic acid methyl ester |
| 11 | OSI-10102 | 3-Amino-2-(2,4-dimethoxybenzoyl)-6-methyl-4-(3,4,5-trimethoxyphenyl)thieno[2,3-b]pyridine-5-carboxylic acid methyl ester |
| 12 | OSI-10185 | 3-Amino-6-methyl-2-(3,4,5-trimethoxybenzoyl)-4-(3,4,5-trimethoxyphenyl)-thieno[2,3-b]pyridine-5-carboxylic acid methyl ester |
| 13 | OSI-10164 | 3-Amino-4-phenyl-2-(4-methoxybenzoyl)-6-methylthieno[2,3-b]pyridine-5-carboxylic acid ethyl ester |
| 14 | OSI-10301 | 3-Amino-4-(4-hydroxyphenyl)-2-(4-methoxybenzoyl)-6-methylthieno[2,3-b]-pyridine-5-carboxylic acid ethyl ester |
| 15 | OSI-10237 | 3-Amino-2-(4-methoxybenzoyl)-4-(3-methoxyphenyl)-6-methylthieno[2,3-b]-pyridine-5-carboxylic acid ethyl ester |
| 16 | OSI-10302 | 3-Amino-4-(4-hydroxy-3-methoxyphenyl)-2-(4-methoxybenzoyl)-6-methyl-thieno[2,3-b]pyridine-5-carboxylic acid ethyl ester |
| 17 | OSI-10214 | 3-Amino-2-(4-methoxybenzoyl)-4-(4-methoxyphenyl)-6-methylthieno[2,3-b]-pyridine-5-carboxylic acid ethyl ester |
| 18 | OSI-9992 | 3-Amino-4-(3,4-dimethoxyphenyl)-2-(4-fluorobenzoyl)-6-methylthieno[2,3-b]-pyridine-5-carboxylic acid ethyl ester |
| 19 | OSI-9994 | 3-Amino-2-(4-chlorobenzoyl)-4-(3,4-dimethoxyphenyl)-6-methylthieno[2,3-b]-pyridine-5-carboxylic acid ethyl ester |
| 20 | OSI-9993 | 3-Amino-4-(3,4-dimethoxyphenyl)-2-(4-methoxybenzoyl)-6-methylthieno[2,3-b]-pyridine-5-carboxylic acid ethyl ester |
| 21 | OSI-9991 | 3-Amino-2-(2,4-dimethoxybenzoyl)-4-(3,4-dimethoxyphenyl)-6-methyl-thieno[2,3-b]pyridine-5-carboxylic acid ethyl ester |
| 22 | OSI-9999 | 3-Amino-2-(4-fluorobenzoyl)-4-(3,4,5-trimethoxyphenyl)-6-methylthieno[2,3-b]-pyridine-5-carboxylic acid ethyl ester |
| 23 | OSI-10034 | 3-Amino-2-(4-chlorobenzoyl)-4-(3,4,5-trimethoxyphenyl)-6-methylthieno[2,3-b]-pyridine-5-carboxylic acid ethyl ester |
| 24 | OSI-9995 | 3-Amino-2-(4-methoxybenzoyl)-6-methyl-4-(3,4,5-trimethoxyphenyl)thieno[2,3-b]-pyridine-5-carboxylic acid ethyl ester |
| 25 | OSI-9767 | 3-Amino-2-(2,4-dimethoxybenzoyl)-6-methyl-4-(3,4,5-trimethoxyphenyl)-thieno[2,3-b]pyridine-5-carboxylic acid ethyl ester |
| 26 | OSI-10266 | 3-Amino-4-(4-ethoxyphenyl)-2-(4-methoxybenzoyl)-6-methylthieno[2,3-b]-pyridine-5-carboxylic acid ethyl ester |
| 27 | OSI-10257 | 3-Amino-4-(4-butoxyphenyl)-2-(4-methoxybenzoyl)-6-methylthieno[2,3-b]-pyridine-5-carboxylic acid ethylester |
| 28 | OSI-10241 | 3-Amino-4-(4-chlorophenyl)-2-(4-methoxybenzoyl)-6-methylthieno[2,3-b]-pyridine-5-carboxylic acid ethylester |
| 29 | OSI-10240 | 3-Amino-4-(4-dimethylaminophenyl)-2-(4-methoxybenzoyl)-6-methylthieno[2,3-b]-pyridine-5-carboxylic acid ethylester |

TABLE 1-continued

Most preferred thieno[2,3-b]pyridines (I).

| Compound No. | Compound name | |
|---|---|---|
| 30 | OSI-10243 | 3-Amino-2-(4-methoxybenzoyl)-6-methyl-4-(3,4,5-trimethoxyphenyl)thieno[2,3-b]-pyridine-5-carboxylic acid butyl ester |
| 31 | OSI-10276 | 3-Amino-2-(4-methoxybenzoyl)-4-(4-methoxyphenyl)-6-methylthieno[2,3-b]-pyridine-5-carboxylic acid 2-methoxyethyl ester |
| 32 | OSI-10267 | 3-Amino-2-benzoyl-6-methyl-4-(3,4,5-trimethoxyphenyl)thieno[2,3-b]pyridine-5-carboxylic acid 2-methoxyethyl ester |
| 33 | OSI-10175 | 3-Amino-2-(3-methoxybenzoyl)-6-methyl-4-(3,4,5-trimethoxyphenyl)thieno[2,3-b]-pyridine-5-carboxylic acid 2-methoxyethyl ester |
| 34 | OSI-10205 | 3-Amino-2-(4-methoxybenzoyl)-6-methyl-4-(3,4,5-trimethoxyphenyl)thieno[2,3-b]-pyridine-5-carboxylic acid 2-methoxyethyl ester |
| 35 | OSI-10206 | 3-Amino-2-(2,4-dimethoxybenzoyl)-6-methyl-4-(3,4,5-trimethoxyphenyl)-thieno[2,3-b]pyridine-5-carboxylic acid 2-methoxyethyl ester |
| 36 | OSI-10268 | 3-Amino-6-methyl-2-(3,4,5-trimethoxybenzoyl)-4-(3,4,5-trimethoxyphenyl)-thieno[2,3-b]pyridine-5-carboxylic acid 2-methoxyethyl ester |
| 37 | OSI-10173 | 3-Amino-2-(2,4-dimethoxybenzoyl)-6-methyl-4-(3,4,5-trimethoxyphenyl)-thieno[2,3-b]pyridine-5-carboxylic acid 2-propoxyethyl ester |
| 38 | OSI-10269 | 3-Amino-6-methyl-2-(3,4,5-trimethoxybenzoyl)-4-(3,4,5-trimethoxyphenyl)-thieno[2,3-b]pyridine-5-carboxylic acid 2-propoxyethylester |
| 39 | OSI-10248 | 3-Amino-4,6-bis-(3,4,5-trimethoxyphenyl)-2-(4-methoxybenzoyl)thieno[2,3-b]-pyridine-5-carboxylic acid ethyl ester |
| 40 | OSI-10281 | 3-Amino-4,6-bis-(3,4,5-trimethoxyphenyl)-2-(3,4,5-trimethoxybenzoyl)-thieno[2,3-b]pyridine-5-carboxylic acid ethyl ester |
| 41 | OSI-10249 | 3-Amino-6-methyl-2-(naphthalene-2-carbonyl)-4-(3,4,5-trimethoxyphenyl)-thieno[2,3-b]pyridine-5-carboxylic acid methyl ester |
| 42 | OSI-10033 | 3-Amino-4-(benzo[1,3]dioxol-5-yl)-2-(4-methoxybenzoyl)-6-methylthieno[2,3-b]-pyridine-5-carboxylic acid ethyl ester |
| 43 | OSI-10279 | 3-Amino-4-(furan-2-yl)-2-(4-methoxybenzoyl)-6-methylthieno[2,3-b]pyridine-5-carboxylic acid ethyl ester |
| 44 | OSI-10280 | 3,6-Diamino-2-(4-methoxybenzoyl)-4-(3,4,5-trimethoxyphenyl)thieno[2,3-b]-pyridine-5-carbonitrile |
| 45 | OSI-10000 | 3-Amino-4,6-dimethyl-2-(2,4-dimetoxybenzoyl)thieno[2,3-b]pyridine |
| 46 | OSI-10291 | 3-Amino-2-(4-methoxybenzoyl)-6-methyl-4-(3,4,5-trimethoxyphenyl)thieno[2,3-b]-pyridine |
| 47 | OSI-10183 | 3-Amino-4,6-bis-(3,4,5-trimethoxyphenyl)-2-(4-chlorobenzoyl)thieno[2,3-b]-pyridine |
| 48 | OSI-10184 | 3-Amino-4,6-bis-(3,4,5-trimethoxyphenyl)-2-(4-methoxybenzoyl)thieno[2,3-b]-pyridine |
| 49 | OSI-10272 | 3-Acetylamino-2-(4-methoxybenzoyl)-6-methyl-4-(3,4,5-trimethoxyphenyl)-thieno[2,3-b]pyridine-5-carboxylic acid 2-methoxyethyl ester |

According to the current invention, the most preferred compounds of formula (II) (intermediates in the synthesis of compounds of formula (I)) are listed in the Table II.

TABLE 2

Most preferred compounds of formula (II)-intermediates in the synthesis of compounds of formula (I).

| Compound No. | |
|---|---|
| 50 | 5-Acetyl-4-(3,4-dimethoxyphenyl)-6-methyl-2-thioxo-1,2-dihydropyridine-3-carbonitrile |
| 51 | 5-Acetyl-6-methyl-2-thioxo-4-(3,4,5-trimethoxyphenyl)-1,2-dihydropyridine-3-carbonitrile |
| 52 | 5-Cyano-4-(3,4-dimethoxyphenyl)-2-methyl-6-thioxo-1,6-dihydropyridine-3-carboxylic acid methyl ester |
| 53 | 5-Cyano-2-methyl-6-thioxo-4-(3,4,5-trimethoxyphenyl)-1,6-dihydropyridine-3-carboxylic acid methyl ester |
| 54 | 5-Cyano-4-(3-methoxyphenyl)-2-methyl-6-thioxo-1,6-dihydropyridine-3-carboxylic acid ethyl ester |
| 55 | 5-Cyano-4-(4-hydroxy-3-methoxyphenyl)-2-methyl-6-thioxo-1,6-dihydropyridine-3-carboxylic acid ethyl ester |
| 56 | 5-Cyano-4-(4-ethoxyphenyl)-2-methyl-6-thioxo-1,6-dihydropyridine-3-carboxylic acid ethyl ester |
| 57 | 4-(4-Butoxyphenyl)-5-cyano-2-methyl-6-thioxo-1,6-dihydropyridine-3-carboxylic acid ethyl ester |
| 58 | 5-Cyano-2-methyl-6-thioxo-4-(3,4,5-trimethoxyphenyl-1,6-dihydropyridine-3-carboxylic acid n-butyl ester |
| 59 | 5-Cyano-2-methyl-6-thioxo-4-(4-methoxyphenyl)-1,6-dihydropyridine-3-carboxylic acid 2-methoxyethyl ester |
| 60 | 5-Cyano-2-methyl-6-thioxo-4-(3,4,5-trimethoxyphenyl)-1,6-dihydropyridine-3-carboxylic acid 2-methoxyethyl ester |
| 61 | 5-Cyano-2-methyl-6-thioxo-4-(3,4,5-trimethoxyphenyl)-1,6-dihydropyridine-3-carboxylic acid 2-propoxyethyl ester |
| 62 | 5-Cyano-2,4-bis-(3,4,5-trimethoxyphenyl)-6-thioxo-1,6-dihydropyridine-3-carboxylic acid ethyl ester |
| 63 | 6-Amino-2-thioxo-4-(3,4,5-trimethoxyphenyl)-1,2-dihydropyridine-3,5-dicarbonitrile |

MDR modulating activity of the preferred thieno[2,3-b]pyridines of formula (I) are summarized in the Table 3.

TABLE 3

MDR modulating activity of the preferred thieno[2,3-b]pyridines of formula (I).

| Compound No. | Compound name | MDR, EC$_{50}$, μM | | | Ca$^{2+}$ A7R5, IC$_{50}$, μM | LD$_{50}$, mg/kg |
|---|---|---|---|---|---|---|
| | | P-gp | MRP1 | BCRP1 | | |
| | Verapamil | 7.1 ± 2.0 | 27.8 ± 0.8 | 37.3 ± 7.0 | 0.3 ± 0.1 | 962 |
| | MK-571 | No effect | 12.4 ± 2.2 | — | No effect | 752 |
| | Glivec | No effect | — | 9.6 ± 1.2 | >100 | 885 |
| 1 | OSI-10036 | 11.5 ± 0.5 | 8.9 ± 1.4 | 9.1 ± 0.1 | 24.0 ± 1.2 | >2000 |
| 2 | OSI-10039 | 13.8 ± 0.3 | 11.8 ± 1.2 | 5.5 ± 0.4 | 15.0 ± 1.1 | >2000 |
| 3 | OSI-10125 | 3.8 ± 0.1 | 6.6 ± 1.0 | 2.6 ± 0.6 | 14.0 ± 0.9 | >2000 |
| 4 | OSI-10120 | 8.5 ± 0.7 | 7.7 ± 0.4 | No effect | No effect | 1073 |
| 5 | OSI-10215 | 4.5 ± 0.2 | No effect | 0.7 ± 0.1 | 15.4 ± 2.0 | >2000 |
| 6 | OSI-9998 | 5.6 ± 0.2 | 11.9 ± 1.3 | 3.6 ± 0.6 | 6.0 ± 0.8 | 2808 |
| 7 | OSI-10106 | 10.3 ± 1.5 | 41.4 ± 1.6 | 4.1 ± 0.9 | 5.6 ± 1.4 | 1045 |
| 8 | OSI-10105 | 11.0 ± 1.0 | 10.4 ± 1.2 | 2.7 ± 0.5 | 3.0 ± 0.8 | >2000 |
| 9 | OSI-10104 | 10.8 ± 1.6 | No effect | 1.4 ± 0.3 | 3.0 ± 0.2 | 1423 |
| 10 | OSI-10103 | 1.5 ± 0.2 | 4.5 ± 0.5 | 4.0 ± 0.8 | 9.0 ± 0.7 | >2000 |
| 11 | OSI-10102 | 6.9 ± 0.9 | 7.1 ± 0.6 | 1.7 ± 0.2 | 18 ± 1.0 | >2000 |
| 12 | OSI-10185 | No effect | No effect | No effect | — | — |
| 13 | OSI-10164 | No effect | No effect | No effect | — | — |
| 14 | OSI-10301 | 26.0 ± 4.2 | 30.7 ± 6.0 | 10.2 ± 1.6 | 4.3 ± 0.7 | 231 |
| 15 | OSI-10237 | No effect | No effect | No effect | — | — |
| 16 | OSI-10302 | 5.3 ± 0.8 | 4.9 ± 0.2 | 3.3 ± 1.1 | 3.7 ± 0.4 | 1872 |
| 17 | OSI-10214 | 6.5 ± 0.9 | No effect | 0.4 ± 0.1 | 100.0 ± 11.0 | >2000 |
| 18 | OSI-9992 | 26.7 ± 0.9 | 22.1 ± 2.0 | 3.0 ± 0.8 | 7.0 ± 1.2 | >2000 |
| 19 | OSI-9994 | 28.4 ± 2.5 | No effect | 5.7 ± 0.9 | 11.0 ± 0.7 | >2000 |
| 20 | OSI-9993 | 9.9 ± 1.6 | 9.4 ± 1.6 | 1.1 ± 0.3 | 3.0 ± 0.4 | 2037 |
| 21 | OSI-9991 | 8.2 ± 1.0 | 8.0 ± 0.2 | 2.0 ± 0.4 | 1.2 ± 0.2 | 2361 |
| 22 | OSI-9999 | 4.0 ± 0.2 | 8.6 ± 0.1 | 1.1 ± 0.4 | 20.0 ± 2.0 | 2938 |
| 23 | OSI-10034 | 3.2 ± 0.7 | 30.4 ± 1.3 | 8.1 ± 1.3 | 4.0 ± 0.4 | 2705 |
| 24 | OSI-9995 | 0.3 ± 0.1 | 5.2 ± 0.6 | 2.5 ± 0.5 | 19 ± 3.0 | >2000 |
| 25 | OSI-9767 | 6.4 ± 0.6 | 12.4 ± 0.4 | 2.6 ± 0.3 | 46 ± 1.4 | >2000 |
| 26 | OSI-10266 | 4.2 ± 0.7 | No effect | 1.3 ± 0.2 | >100 | >2000 |
| 27 | OSI-10257 | No effect | No effect | No effect | — | — |
| 28 | OSI-10241 | 10.0 ± 0.2 | No effect | 2.7 ± 0.6 | >100 | >2000 |
| 29 | OSI-10240 | 1.8 ± 0.6 | No effect | 0.5 ± 0.1 | 35.0 ± 3.0 | >2000 |
| 30 | OSI-10243 | 1.5 ± 0.1 | No effect | 0.4 ± 0.08 | 5.0 ± 0.7 | >2000 |
| 31 | OSI-10276 | 1.0 ± 0.1 | No effect | 0.8 ± 0.1 | 21.0 ± 4.0 | >2000 |
| 32 | OSI-10267 | 1.4 ± 0.1 | 3.9 ± 0.6 | 1.3 ± 0.2 | 2.2 ± 0.3 | >2000 |
| 33 | OSI-10175 | 1.3 ± 0.1 | No effect | 1.2 ± 0.3 | 6.2 ± 0.7 | >2000 |
| 34 | OSI-10205 | 0.3 ± 0.2 | 1.1 ± 0.1 | 0.2 ± 0.05 | 3.1 ± 0.4 | 2097 |
| 35 | OSI-10206 | 2.0 ± 0.0 | 7.0 ± 1.0 | 2.5 ± 0.5 | 9.0 ± 1.0 | 2983 |
| 36 | OSI-10268 | No effect | No effect | No effect | — | — |
| 37 | OSI-10173 | 0.6 ± 0.1 | No effect | 0.6 ± 0.1 | >100 | >2000 |
| 38 | OSI-10269 | No effect | No effect | No effect | — | — |
| 39 | OSI-10248 | 22.0 ± 0.5 | No effect | 3.0 ± 0.3 | No effect | >2000 |
| 40 | OSI-10281 | 3.4 ± 0.4 | No effect | 0.4 ± 0.1 | No effect | >2000 |
| 41 | OSI-10249 | 10.5 ± 0.7 | No effect | 0.8 ± 0.2 | 18.0 ± 1.4 | >2000 |
| 42 | OSI-10033 | 20.4 ± 0.1 | 24.8 ± 1.2 | 2.3 ± 0.4 | 18.0 ± 1.0 | 2011 |
| 43 | OSI-10279 | No effect | No effect | No effect | — | — |
| 44 | OSI-20280 | No effect | No effect | No effect | — | — |
| 45 | OSI-10000 | No effect | No effect | No effect | — | 959 |
| 46 | OSI-10291 | No effect | No effect | No effect | — | — |
| 47 | OSI-10183 | 31.4 ± 0.8 | No effect | 14.5 ± 3.5 | — | >2000 |
| 48 | OSI-10184 | 32.5 ± 2.1 | No effect | No effect | No effect | 3084 |
| 49 | OSI-10272 | No effect | No effect | No effect | — | — |

The following examples are illustrating but not restricting the present invention.

Reagents and solvents used below can be obtained from commercial sources. $^1$H NMR spectra were recorded on a Varian Mercury 200 MHz and Varian Mercury 400 MHz NMR spectrometer. The $^1$H chemical shifts are reported in ppm relative to HMDSO. Significant peaks are tabulated in the order: number of protons and multiplicity (s, singlet; d, doublet; t, triplet; q, quartet; qui, quintet; se, sextet, m, multiplet; br.s, broad singlet), coupling constant(s) in Hertz (Hz). Melting points were determined on OptiMelt MPA100 apparatus and are uncorrected.

General Method for Preparation of thieno[2,3-b]pyridines (I-1) from Intermediates (II-1)

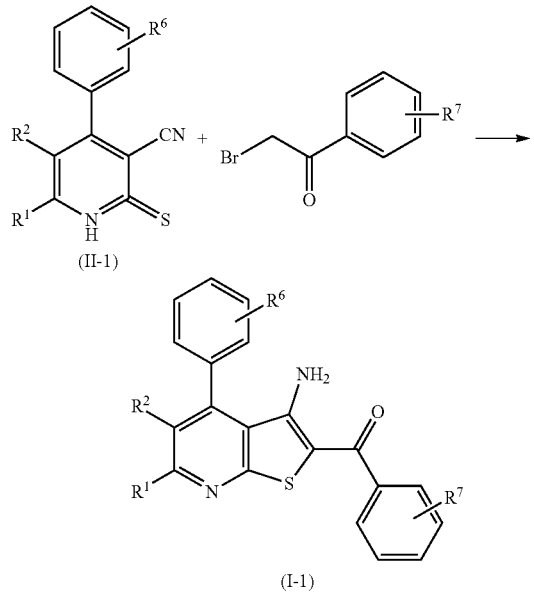

(II-1)

(I-1)

Reagents and conditions:
1) 2.4 equiv 3M NaOH/$H_2O$, rt, 10 min, EtOH;
2) 2-bromoacethophenone, 78° C., 2-3 min, then rt, 30 min, 39-96%

To solution of 5-acetyl-4-(3,4-dimethoxyphenyl)-6-methyl-2-thioxo-1,6-dihydropyridine-3-carbonitrile (50) (0.16 g, 0.5 mmol) in 10 ml of ethanol 3M sodium hydroxide water solution (0.4 ml, 1.2 mmol) was added. The reaction mixture was shortly refluxed to form thiolate. Then 2-bromo-4'-methoxyacetophenone (0.11 g, 0.5 mmol) was added, the reaction mixture was refluxed for 5 min and stirred at room temperature for 30 min. The precipitated crystals were separated by filtration and purified by washing with ethanol and water during the filtration to give 0.21 g (91%) of 5-acetyl-3-amino-4-(3,4-dimethoxyphenyl)-2-(4-methoxybenzoyl)-6-methylthieno[2,3-b]pyridine (1) (general formula (I-1)).

In a similar manner thieno[2,3-b]pyridines 2-40 (general formula (I-1)) have been prepared starting from original 6-thioxo-1,6-dihydropyridines (yield, melting points and $^1$H NMR data are combined in tables 4 and 5) or from 6-thioxo-1,6-dihydropyridines prepared according to literature data. The yields, melting points and $^1$H NMR data of thieno[2,3-b]pyridines (general formula (I-1)) are combined in tables 4 and 5.

TABLE 4

Yields (general procedure) and melting points of thieno[2,3-b]pyridines (I-1).

| Compound No. | Compound name | $R^1$ | $R^2$ | $R^6$ | $R^7$ | Yield, % | Mp, ° C. |
|---|---|---|---|---|---|---|---|
| 1 | OSI-10036 | Me | COMe | 3,4-$(OMe)_2$ | 4-OMe | 91 | 176-178 |
| 2 | OSI-10039 | Me | COMe | 3,4-$(OMe)_2$ | 2,4-$(OMe)_2$ | 85 | 182-184 |
| 3 | OSI-10125 | Me | COMe | 3,4,5-$(OMe)_3$ | 4-OMe | 72 | 162-164 |
| 4 | OSI-10120 | Me | COMe | 3,4,5-$(OMe)_3$ | 2,4-$(OMe)_2$ | 61 | 160-162 |
| 5 | OSI-10215 | Me | COOMe | 4-OMe | 4-OMe | 78 | 179-180 |
| 6 | OSI-9998 | Me | COOMe | 3,4-$(OMe)_2$ | 4-OMe | 84 | 192-194 |
| 7 | OSI-10106 | Me | COOMe | 3,4-$(OMe)_2$ | 2,4-$(OMe)_2$ | 42 | 168-169 |
| 8 | OSI-10105 | Me | COOMe | 3,4,5-$(OMe)_3$ | 4-F | 89 | 195-196 |
| 9 | OSI-10104 | Me | COOMe | 3,4,5-$(OMe)_3$ | 4-Cl | 87 | 190-191 |
| 10 | OSI-10103 | Me | COOMe | 3,4,5-$(OMe)_3$ | 4-OMe | 74 | 190-191 |
| 11 | OSI-10102 | Me | COOMe | 3,4,5-$(OMe)_3$ | 2,4-$(OMe)_2$ | 87 | 138-139 |
| 12 | OSI-10185 | Me | COOMe | 3,4,5-$(OMe)_3$ | 3,4,5-$(OMe)_3$ | 86 | 197-198 |
| 13 | OSI-10164 | Me | COOEt | H | 4-OMe | 92 | 150-152 |
| 14 | OSI-10301 | Me | COOEt | 4-OH | 4-OMe | 39 | 196-198 |
| 15 | OSI-10237 | Me | COOEt | 3-OMe | 4-OMe | 88 | 134-136 |
| 16 | OSI-10302 | Me | COOEt | 3-OMe, 4-OH | 4-OMe | 67 | 201-203 |
| 17 | OSI-10214 | Me | COOEt | 4-OMe | 4-OMe | 86 | 150-151 |
| 18 | OSI-9992 | Me | COOEt | 3,4-$(OMe)_2$ | 4-F | 92 | 204-206 |
| 19 | OSI-9994 | Me | COOEt | 3,4-$(OMe)_2$ | 4-Cl | 90 | 178-180 |
| 20 | OSI-9993 | Me | COOEt | 3,4-$(OMe)_2$ | 4-OMe | 92 | 188-190 |
| 21 | OSI-9991 | Me | COOEt | 3,4-$(OMe)_2$ | 2,4-$(OMe)_2$ | 88 | 176-178 |
| 22 | OSI-9999 | Me | COOEt | 3,4,5-$(OMe)_3$ | 4-F | 92 | 193-195 |
| 23 | OSI-10034 | Me | COOEt | 3,4,5-$(OMe)_3$ | 4-Cl | 89 | 189-191 |
| 24 | OSI-9995 | Me | COOEt | 3,4,5-$(OMe)_3$ | 4-OMe | 89 | 204-206 |
| 25 | OSI-9767 | Me | COOEt | 3,4,5-$(OMe)_3$ | 2,4-$(OMe)_2$ | 96 | 174-176 |
| 26 | OSI-10266 | Me | COOEt | 4-OEt | 4-OMe | 96 | 150-151 |
| 27 | OSI-10257 | Me | COOEt | 4-OBu(n) | 4-OMe | 89 | 105-106 |
| 28 | OSI-10241 | Me | COOEt | 4-Cl | 4-OMe | 93 | 139-140 |
| 29 | OSI-10240 | Me | COOEt | 4-$NMe_2$ | 4-OMe | 91 | 170-171 |
| 30 | OSI-10243 | Me | COOBu(n) | 3,4,5-$(OMe)_3$ | 4-OMe | 93 | 149-150 |
| 31 | OSI-10276 | Me | $COOC_2H_4OMe$ | 4-OMe | 4-OMe | 90 | 125-126 |
| 32 | OSI-10267 | Me | $COOC_2H_4OMe$ | 3,4,5-$(OMe)_3$ | H | 90 | 100-101 |
| 33 | OSI-10175 | Me | $COOC_2H_4OMe$ | 3,4,5-$(OMe)_3$ | 3-OMe | 78 | 131-132 |
| 34 | OSI-10205 | Me | $COOC_2H_4OMe$ | 3,4,5-$(OMe)_3$ | 4-OMe | 82 | 154-155 |
| 35 | OSI-10206 | Me | $COOC_2H_4OMe$ | 3,4,5-$(OMe)_3$ | 2,4-$(OMe)_2$ | 92 | 129-131 |
| 36 | OSI-10268 | Me | $COOC_2H_4OMe$ | 3,4,5-$(OMe)_3$ | 3,4,5-$(OMe)_3$ | 81 | 172-173 |
| 37 | OSI-10173 | Me | $COOC_2H_4OPr(n)$ | 3,4,5-$(OMe)_3$ | 4-OMe | 77 | 79-80 |
| 38 | OSI-10269 | Me | $COOC_2H_4OPr(n)$ | 3,4,5-$(OMe)_3$ | 3,4,5-$(OMe)_3$ | 72 | 155-156 |

TABLE 4-continued

Yields (general procedure) and melting points of thieno[2,3-b]pyridines (I-1).

| Compound No. | Compound name | $R^1$ | $R^2$ | $R^6$ | $R^7$ | Yield, % | Mp, °C. |
|---|---|---|---|---|---|---|---|
| 39 | OSI-10248 | 3,4,5-(OMe)$_3$C$_6$H$_2$ | COOEt | 3,4,5-(OMe)$_3$ | 4-OMe | 95 | 196-197 |
| 40 | OSI-10281 | 3,4,5-(OMe)$_3$C$_6$H$_2$ | COOEt | 3,4,5-(OMe)$_3$ | 3,4,5-(OMe)$_3$ | 90 | 178-179 |

$^1$H NMR (400 MHz) spectra of compounds of formula (I) which include compounds of formula (I-1) and (I-2) are combined in Table 5.

TABLE 5

$^1$H NMR spectra of thieno[2,3-b]pyridines (I)

| Compound No. | Compound name | $^1$H NMR spectra of compounds of formula (I) |
|---|---|---|
| 1 | OSI-10036 | (CDCl$_3$) δ 2.02 (3H, s, COMe), 2.60 (3H, s, Me); 3.88, 3.89 and 3.98 (3H, 3H and 3H, s, s and s, C$_6$H$_3$(OMe)$_2$ and C$_6$H$_4$OMe); 6.76 (2H, br.s, NH$_2$), 6.88, 6.94-7.03, 7.87 (1H, 4H, 2H, d, J = 1.6 Hz, m, d, J = 8.6 Hz, C$_6$H$_3$(OMe)$_2$ and C$_6$H$_4$OMe) |
| 2 | OSI-10039 | (CDCl$_3$) δ 2.01 (3H, s, COMe); 2.58 (3H, s, Me); 3.82, 3.87, 3.89 and 3.98 (3H, 3H, 3H and 3H, s, s, s and s, 2xC$_6$H$_3$(OMe)$_2$); 6.70 (2H, br.s, NH$_2$); 6.52-6.55, 6.87-7.02, 7.37 (2H, 3H and 1H, m, m and d, J = 8.6 Hz, 2xC$_6$H$_3$(OMe)$_2$) |
| 3 | OSI-10125 | (CDCl$_3$) δ 2.06 (3H, s, COMe); 2.60 (3H, s, Me); 3.86, 3.88 and 3.95 (6H, 3H and 3H, s, s and s, C$_6$H$_4$OMe and C$_6$H$_2$(OMe)$_3$); 6.79 (2H, br.s, NH$_2$); 6.59, 6.97 and 7.87 (2H, 2H and 2H, s, d, J = 8.6 Hz, and d, J = 8.6 Hz, C$_6$H$_2$(OMe)$_3$ and C$_6$H$_4$OMe) |
| 4 | OSI-10120 | (CDCl$_3$) δ 2.05 (3H, s, COMe); 2.58 (3H, s, Me); 3.82, 3.87and 3.95 (3H, 9H and 3H, s, s and s, C$_6$H$_3$(OMe)$_2$ and C$_6$H$_2$(OMe)$_3$); 6.77 (2H, br.s, NH$_2$); 6.53-6.55, 6.59 and 7.38 (2H, 2H and 1H, m, s, and d, J = 8.2 Hz, C$_6$H$_2$(OMe)$_3$ and C$_6$H$_3$(OMe)$_2$) |
| 5 | OSI-10215 | (CDCl$_3$) δ 2.67 (3H, s, Me); 3.58 (3H, s, COOMe); 3.88 and 3.90 (3H and 3H, s and s, 2x C$_6$H$_4$OMe; 6.68 (2H, br.s, NH$_2$); 6.97, 7.04, 7.32 and 7.86 (2H, 2H, 2H and 2H, d, d, d, and d, J = 8.6 Hz, 2xC$_6$H$_4$OMe) |
| 6 | OSI-9998 | (CDCl$_3$) δ 2.61 (3H, s, Me); 3.54 (3H, s, COOMe) 3.82, 3.83 and 3.91 (3H, 3H and 3H, s, s and s, C$_6$H$_3$(OMe)$_2$ and C$_6$H$_4$OMe); 6.67 (2H, br.s, NH$_2$), 6.83-6.95, 6.91 and 7.80 (3H, 2H and 2H, m, d and d, J = 8.6 Hz, C$_6$H$_3$(OMe)$_2$ and C$_6$H$_4$OMe) |
| 7 | OSI-10106 | (CDCl$_3$) δ 2.58 (3H, s, Me); 3.53 (3H, s, COOMe); 3.75, 3.80, 3.83 and 3.91 (3H, 3H, 3H and 3H, s, s, s, and s, 2xC$_6$H$_3$(OMe)$_2$); 6.45-6.48, 6.82-6.94 and 7.20 (2H, 3H and 1H, m, m and d, J = 8.6 Hz, 2xC$_6$H$_3$(OMe)$_2$); 6.64 (2H, br.s. NH$_2$) |
| 8 | OSI-10105 | (CDCl$_3$) δ 2.62 (3H, s, Me); 3.56 (3H, s, COOMe); 3.80 and 3.90 (6H and 3H, s and s, C$_6$H$_2$(OMe)$_3$); 6.54, 7.07-7.12, and 7.82 (2H, 2H and 2H, s, m and m, C$_6$H$_2$(OMe)$_3$ and C$_6$H$_4$F); 6.80 (2H, br.s, NH$_2$) |
| 9 | OSI-10104 | (CDCl$_3$) δ 2.61 (3H, s, Me); 3.56 (3H, s, COOMe); 3.80 and 3.90 (6H and 3H, s and s, C$_6$H$_2$(OMe)$_3$); 6.54, 7.40 and 7.73 (2H, 2H and 2H, s, d and d, J = 8.6 Hz C$_6$H$_2$(OMe)$_3$ and C$_6$H$_4$Cl); 6.78 (2H, br.s, NH$_2$) |
| 10 | OSI-10103 | (CDCl$_3$) δ 2.61 (3H, s, Me); 3.56 (3H, s, COOMe); 3.80, 3.82 3.88 (6H and 3H, 3H, s, s and s, C$_6$H$_2$(OMe)$_3$ and C$_6$H$_4$OMe); 6.54, 6.90 and 7.81 (2H, 2H and 2H, s, d and d, J = 8.2 Hz C$_6$H$_2$(OMe)$_3$ and C$_6$H$_4$OMe); 6.70 (2H, br.s, NH$_2$) |
| 11 | OSI-10102 | (CDCl$_3$) δ 2.58 (3H, s, Me); 3.56 (3H, s, COOMe); 3.75 3.80 and 3.87 (3H, 9H and 3H, s, s and s, C$_6$H$_3$(OMe)$_2$ and C$_6$H$_2$(OMe)$_3$); 6.46-6.48, 6.53 and 7.31 (2H, 2H and 1H, m, s and d J = 7.8 Hz, C$_6$H$_3$(OMe)$_2$ and C$_6$H$_2$(OMe)$_3$); 6.77 (2H, br.s, NH$_2$) |
| 12 | OSI-10185 | (CDCl$_3$) δ 2.67 (3H, s, Me), 3.61 (3H, s, COOMe); 3.85, 3.91 and 3.94 (6H, 9H, 3H, s, s and s, C$_6$H$_2$(OMe)$_3$ and C$_6$H$_2$(OMe)$_3$); 6.59 and 7.14 (2H and 2H, s and s, C$_6$H$_2$(OMe)$_3$ and C$_6$H$_2$(OMe)$_3$); 6.78 (2H, br.s, NH$_2$) |
| 13 | OSI-10164 | (CDCl$_3$) δ 0.94 and 4.01 (3H and 2H, t and q, J = 7.0 Hz, COOEt); 2.70 (3H, s, Me); 3.88 (3H, s, C$_6$H$_4$OMe); 6.57 (2H, br.s, NH$_2$); 6.97, 7.41-7.54 and 7.86 (2H, 5H and 2H, d, m, d, J = 8.6 Hz, C$_6$H$_4$OMe and C$_6$H$_5$) |
| 14 | OSI-10301 | (DMSO-d$_6$) δ 0.89 and 3.98 (5H, t and q, J = 7.0 Hz, COOEt); 2.54 (3H, s, Me); 3.81 (3H, s, C$_6$H$_4$OMe); 6.69 (2H, s, NH$_2$); 6.90, 7.04, 7.18 and 7.73 (2H, 2H, 2H and 2H, d, d, d and d, J = 8.6 Hz, C$_6$H$_4$OH and C$_6$H$_4$OMe); 9.97 (1H, s, C$_6$H$_4$OH). |
| 15 | OSI-10237 | (CDCl$_3$) δ 0.99 and 4.05 (3H and 2H, t and q, J = 7.0 Hz, COOEt); 2.70 (3H, s, Me); 3.84 and 3.88 (3H and 3H, s and s, 2xC$_6$H$_4$OMe); 6.70 (2H, br.s, NH$_2$); 6.92, |

TABLE 5-continued

¹H NMR spectra of thieno[2,3-b]pyridines (I)

| Compound No. | Compound name | ¹H NMR spectra of compounds of formula (I) |
|---|---|---|
| | | 6.96-6.99, 7.06, 7.43, 7.86 (1H, 3H, 1H, 1H and 2H, t, J = 2.3 Hz, m, dd, J = 2.3 Hz, J = 8.2 Hz, t, J = 8.2 Hz, d, J = 8.6 Hz, 2xC$_6$H$_4$OMe) |
| 16 | OSI-10302 | (DMSO-d$_6$) δ 0.91 and 4.00 (5H, t and q, J = 7.0 Hz, COOEt); 2.19 (3H, s, Me); 3.70 and 3.84 (3H and 3H, s and s, C$_6$H$_4$OMe and C$_6$H$_3$OMe); 6.74 (2H, s, NH$_2$), 6.87-6.93, 7.06 and 8.04 (3H, 2H and 2H, m, d and d, J = 9.0 Hz, C$_6$H$_3$OMeOH and C$_6$H$_4$OMe) |
| 17 | OSI-10214 | (CDCl$_3$) δ 1.02 and 4.06 (3H and 2H, t and q, J = 7.0 Hz, COOEt); 2.68 (3H, s, Me); 3.88 and 3.89 (3H and 3H, s and s, 2xC$_6$H$_4$OMe); 6.67 (2H, br.s, NH$_2$); 6.97, 7.04, 7.33 and 7.86 (2H, 2H, 2H and 2H, d, d, d and, J = 8.6 Hz, 2xC$_6$H$_4$OMe) |
| 18 | OSI-9992 | (CDCl$_3$) δ 0.97 and 4.01 (3H and 2H, t and q, J = 7.0 Hz, COOEt); 2.62 (3H, s, Me); 3.83 and 3.91 (3H and 3H, s and s, C$_6$H$_3$(OMe)$_2$); 6.70 (2H, br.s, NH$_2$); 6.90-6.97, 6.99, 7.15 and 7.84-7.87(1H, 2H, 2H and 2H, m, t, J = 8.6 Hz and m, C$_6$H$_3$(OMe)$_2$ and C$_6$H$_4$F) |
| 19 | OSI-9994 | (CDCl$_3$) δ 0.97 and 4.01 (3H and 2H, t and q, J = 7.0 Hz, COOEt); 2.62 (3H, s, Me); 3.83 and 3.91 (3H and 3H, s and s, C$_6$H$_3$(OMe)$_2$); 6.70 (2H, br.s, NH$_2$); 6.83-6.95, 7.38 and 7.71 (3H, 2H and 2H, m, d and d, J = 8.6 Hz, C$_6$H$_3$(OMe)$_2$ and C$_6$H$_4$Cl) |
| 20 | OSI-9993 | (CDCl$_3$) δ 0.97 and 4.01 (3H and 2H, t and q, J = 7.0 Hz, COOEt); 2.62 (3H, s, Me); 3.82 (3H and 3H, s and s, C$_6$H$_3$(OMe)$_2$); 3.91 (3H, s, C$_6$H$_4$OMe) 6.64 (2H, br.s, NH$_2$); 6.84-6.93, 6.92 and 7.80 (3H, 2H and 2H, m, d and d, J = 8.6 Hz, C$_6$H$_3$(OMe)$_2$ and C$_6$H$_4$OMe) |
| 21 | OSI-9991 | (CDCl$_3$) δ 0.96 and 3.89 (3H and 2H, t and q, J = 7.0 Hz, COOEt); 2.60 (3H, s, Me); 3.75, 3.80, 3.83 and 3.90 (3H, 3H, 3H and 3H, s, s, s and s, 2xC$_6$H$_3$(OMe)$_2$); 6.46-6.48, 6.83-6.92 and 7.30-7.32 (3H, 3H and 2H, m, m and m, 2xC$_6$H$_3$(OMe)$_2$) and NH$_2$) |
| 22 | OSI-9999 | (CDCl$_3$) δ 0.96 and 4.03 (3H and 2H, t and q, J = 7.0 Hz, COOEt); 2.63 (3H, s, Me); 3.80 and 3.87 (6H and 3H, s and s, C$_6$H$_2$(OMe)$_3$); 6.55, 7.09 and 7.80 (2H, 2H and 2H, s, t and t, J = 8.6 Hz, C$_6$H$_2$(OMe)$_3$ and, C$_6$H$_4$F), 6.77 (2H, br.s, NH$_2$) |
| 23 | OSI-10034 | (CDCl$_3$) δ 0.96 and 4.03 (3H and 2H, t and q, J = 7.0 Hz, COOEt); 2.63 (3H, s, Me); 3.80 and 3.87 (6H and 3H, s and s, C$_6$H$_2$(OMe)$_3$); 6.55, 6.91 and 7.80 (2H, 2H and 2H, s, d and d, J = 8.6 Hz, C$_6$H$_2$(OMe)$_3$ and C$_6$H$_4$Cl), 6.79 (2H, br.s, NH$_2$) |
| 24 | OSI-9995 | (CDCl$_3$) δ 0.96 and 4.02 (3H and 2H, t and q, J = 7.0 Hz, COOEt); 2.63 (3H, s, Me); 3.80, 3.83 and 3.87 (6H, 3H and 3H, s, s and s, C$_6$H$_2$(OMe)$_3$ and C$_6$H$_4$OMe); 6.55, 6.91 and 7.80 (2H, 2H and 2H, s, d and d, J = 8.6 Hz, C$_6$H$_2$(OMe)$_3$ and C$_6$H$_4$OMe), 6.70 (2H, s, NH$_2$) |
| 25 | OSI-9767 | (CDCl$_3$) δ 0.95 and 4.01 (3H and 2H, t and q, J = 7.0 Hz, COOEt); 2.60 (3H, s, Me); 3.75, 3.80 and 3.86 (3H, 9H and 3H, s, s and s, C$_6$H$_2$(OMe)$_3$ and C$_6$H$_3$(OMe)$_2$); 6.45-6.54 and 7.29-7.33 (2H and 3H, m and m, C$_6$H$_2$(OMe)$_3$ and C$_6$H$_3$(OMe)$_2$) |
| 26 | OSI-10266 | (CDCl$_3$) δ 1.02 and 4.06 (3H and 2H, t and q, J = 7.4 Hz, C$_6$H$_4$OEt); 1.48 and 4.11 (3H and 2H, t and q, J = 7.0 Hz, COOEt); 2.68 (3H, s, Me); 3.88 (3H, s, C$_6$H$_4$OMe); 6.66 (2H, br.s, NH$_2$); 6.97, 7.02, 7.31 and 7.86 (2H, 2H, 2H and 2H, d, d, d and d, J = 8.6 Hz, C$_6$H$_4$OMe and C$_6$H$_4$OEt) |
| 27 | OSI-10257 | (CDCl$_3$) δ 0.99-1.04, 1.49-1.59, 1.79-1.86 and 4.02-4.09 (6H, 2H, 2H and 4H, m, m, m, m, COOEt and C$_6$H$_4$OBu); 2.68 (3H, s, Me); 3.88 (3H, s, C$_6$H$_4$OMe); 6.67 (2H, br.s, NH$_2$); 6.97, 7.02, 7.31 and 7.86 (2H, 2H, 2H and 2H, d, d, d and d, J = 8.6 Hz, C$_6$H$_4$OMe and C$_6$H$_4$OBu) |
| 28 | OSI-10241 | (CDCl$_3$) δ 1.02 and 4.06 (3H and 2H, t and q, J = 7.0 Hz, COOEt); 2.70 (3H, s, Me); 3.89 (3H, s, C$_6$H$_4$OMe); 6.54 (2H, br.s, NH$_2$); 6.97, 7.37, 7.52 and 7.86 (2H, 2H, 2H and 2H, d, d, d and d, J = 8.6 Hz, C$_6$H$_4$OMe and C$_6$H$_4$Cl) |
| 29 | OSI-10240 | (CDCl$_3$) δ 1.04 and 4.08 (3H and 2H, t and q, J = 7.0 Hz, COOEt); 2.67 (3H, s, Me); 3.04 (6H, s, NMe$_2$); 3.88 (3H, s, C$_6$H$_4$OMe); 6.78, 6.96, 7.23 and 7.86 (2H, 2H, 2H and 2H, d, d, d and d, J = 8.6 Hz, C$_6$H$_4$OMe and C$_6$H$_6$NMe$_2$); 6.82 (2H, br.s, NH$_2$) |
| 30 | OSI-10243 | (CDCl$_3$) δ 0.85, 1.20, 1.38 and 4.02 (3H, 2H, 2H and 2H, t, se, J = 7.4 Hz, qui, t, J = 6.7 Hz, COOBu); 2.69 (3H, s, Me); 3.86, 3.89 and 3.94 (6H, 3H and 3H, s, s and s, C$_6$H$_2$(OMe)$_3$ and C$_6$H$_4$OMe); 6.61, 6.97 and 7.87 (2H, 2H and 2H, s, d and d, J = 8.6 Hz, C$_6$H$_4$(OMe) and C$_6$H$_2$(OMe)$_3$); 6.77 (2H, br.s, NH$_2$) |
| 31 | OSI-10276 | (CDCl$_3$) δ 2.69 (3H, s, Me); 3.30, 3.36 and 4.15 (3H, 2H and 2H, s, t and t, J = 4.7 Hz COO(CH$_2$)$_2$OMe); 3.88 and 3.90 (3H and 3H, s and s, 2xC$_6$H$_4$OMe); 6.64 (2H, br.s, NH$_2$); 6.97, 7.04, 7.34 and 7.86 (2H, 2H, 2H and 2H, d, d, d and d, J = 8.6 Hz, 2xC$_6$H$_4$OMe) |

TABLE 5-continued

$^1$H NMR spectra of thieno[2,3-b]pyridines (I)

| Compound No. | Compound name | $^1$H NMR spectra of compounds of formula (I) |
|---|---|---|
| 32 | OSI-10267 | (CDCl$_3$) δ 2.69 (3H, s, Me); 3.28, 3.35 and 4.17 (3H, 2H and 2H, s, t and t, J = 4.7 Hz COO(CH$_2$)$_2$OMe); 3.87 and 3.95 (6H and 3H; s and s, C$_6$H$_2$(OMe)$_3$); 6.62, 7.46-7.55 and 7.83 (2H, 3H and 2H, s, m and d, J = 8.2 Hz, C$_6$H$_2$(OMe)$_3$ and C$_6$H$_5$); 6.82 (2H, br.s, NH$_2$) |
| 33 | OSI-10175 | (CDCl$_3$) δ 2.70 (3H, s, Me); 3.28, 3.35 and 4.17 (3H, 2H and 2H, s, t and t, J = 4.7 Hz,COO(CH$_2$)$_2$OMe); 3.87 and 3.95 (9H and 3H, s and s, C$_6$H$_2$(OMe)$_3$ and C$_6$H$_4$OMe); 6.62, 7.06-7.08 and 7.34-7.44 (2H, 1H and 3H, s, m and m, C$_6$H$_4$OMe and C$_6$H$_2$(OMe)$_3$) |
| 34 | OSI-10205 | (CDCl$_3$) δ 2.70 (3H, s, Me), 3.28, 3.35 and 4.17 (3H, 2H and 2H, s, t and t, J = 4.7 Hz, COO(CH$_2$)$_2$OMe), 3.87, 3.89 and 3.95 (6H, 3H and 3H, s, s and s, C$_6$H$_2$(OMe)$_3$ and C$_6$H$_4$OMe), 6.62, 6.97 and 7.87 (2H, 2H and 2H, s, d and d, J = 8.6 Hz C$_6$H$_2$(OMe)$_3$ and C$_6$H$_4$OMe), 6.78 (2H, br.s, NH$_2$) |
| 35 | OSI-10206 | (CDCl$_3$) δ 2.67 (3H, s, Me); 3.2, 3.27 and 4.16 (3H, 2H and 2H, s, t and t, J = 4.7 Hz, COO(CH$_2$)$_2$OMe), 3.82, 3.87 and 3.94 (3H, 9H and 3H, s, s and s, C$_6$H$_2$(OMe)$_3$ and C$_6$H$_3$(OMe)$_2$), 6.52-6.55, 6.60 and 7.38 (2H, 2H and 1H, m, s and d, J = 8.2 Hz, C$_6$H$_3$(OMe)$_2$ and C$_6$H$_2$(OMe)$_3$) 6.72 (2H, br.s, NH$_2$) |
| 36 | OSI-10268 | (CDCl$_3$) δ 2.71 (3H, s, Me); 3.29, 3.55 and 4.18 (3H, 2H and 2H, s, t and t, J = 4.7 Hz, COO(CH$_2$)$_2$OMe); 3.87, 3.92 and 3.95 (6H, 9H and 3H, s, s and s, 2xC$_6$H$_2$(OMe)$_3$); 6.62 and 7.15 (2H and 2H, s and s, 2xC$_6$H$_2$(OMe)$_3$) |
| 37 | OSI-10173 | (CDCl$_3$) δ 0.89, 1.51-1.59, 3.33, 3.41 and 4.17 (3H, 2H, 2H, 2H and 2H, t, J = 7.4 Hz, m, t, J = 6.7 Hz, t and t, J = 4.7 Hz, COO(CH$_2$)$_2$OPr); 2.70 (3H, s, Me); 3.86, 3.89 and 3.95 (6H, 3H and 3H, s, s and s, C$_6$H$_2$(OMe)$_3$ and C$_6$H$_4$OMe); 6.62, 6.97 and 7.87 (2H, 2H and 2H, s, d and d, J = 8.6 C$_6$H$_2$(OMe)$_3$ and C$_6$H$_4$OMe); 6.78 (2H, br.s, NH$_2$) |
| 38 | OSI-10269 | (CDCl$_3$) δ 0.89, 1.51-1.60, 3.34, 3.42 and 4.18 (3H, 2H, 2H, 2H and 2H, t, J = 7.4 Hz, m, t, J = 6.7 Hz, t and t, J = 4.7 Hz, COO(CH$_2$)$_2$OPr); 2.71 (3H, s, Me); 3.87, 3.93 and 3.95 (6H, 9H, 3H, s, s and s, 2xC$_6$H$_2$(OMe)$_3$); 6.62 and 7.15 (2H and 2H, s and s, 2xC$_6$H$_2$(OMe)$_3$); 6.86 (2H, br.s, NH$_2$) |
| 39 | OSI-10248 | (CDCl$_3$) δ 0.87 and 3.94 (3H and 2H, t and q, J = 7.4 Hz, COOEt); 3.86, 3.87, and 3.89 (9H, 9H and 3H, br.s, br.s and s, 2xC$_6$H$_2$(OMe)$_3$ and C$_6$H$_4$OMe); 6.65, 6.96, 6.98 and 7.87 (2H, 2H, 2H and 2H, s, s, d and d, J = 9.0 Hz, 2xC$_6$H$_2$(OMe)$_3$ and C$_6$H$_4$OMe); 6.75 (2H, br.s, NH$_2$) |
| 40 | OSI-10281 | (CDCl$_3$) δ 0.83 and 3.94 (3H and 2H, t and q, J = 7.0 Hz COOEt); 3.59, 3.86, 3.87, 3.88, 3.92 and 3.93 (6H, 3H, 6H, 9H and 3H, br.s, br.s, br.s, br.s and br.s, 3xC$_6$H$_2$(OMe)$_3$); 6.65, 6.95 and 7.15 (2H, 2H and 2H, s, s and s, 3xC$_6$H$_2$(OMe)$_3$); 6.80 (2H, br.s, NH$_2$) |
| 41 | OSI-10249 | (CDCl$_3$) δ 2.66 (3H, s, Me); 3.62 (3H, s, COOMe); 3.86 and 3.94 (6H and 3H, s and s, C$_6$H$_2$(OMe)$_3$); 6.61 (2H, s, C$_6$H$_2$(OMe)$_3$); 7.56-7.60, 7.87-7.94 and 8.39 (2H, 4H and 1H, m, m and s, C$_{10}$H$_7$); 6.76 (2H, br.s, NH$_2$) |
| 42 | OSI-10033 | (CDCl$_3$) δ 1.09 and 4.12 (3H and 2H, t and q, J = 7.0 Hz, COOEt); 2.68 (3H, s, CH$_3$); 3.88 (3H, s, C$_6$H$_4$OMe); 6.09 (2H, d, J = 7.4 Hz, C$_6$H$_3$(O$_2$CH$_2$)); 6.73 (2H, br.s, NH$_2$); 6.85-6.98, 7.86 (7H, m, d, J = 8.6 Hz, C$_6$H$_3$(O$_2$CH$_2$) and C$_6$H$_4$OMe)) |
| 43 | OSI-10279 | (DMSO-d$_6$) δ 1.08 and 4.14 (5H, t and q, J = 7.0 Hz, COOEt); 2.57 (3H, s, CH$_3$); 3.83 (3H, s, C$_6$H$_4$OMe); 6.76 and 6.77, 6.87 and 8.02 (1H, 1H and 1H, dd, J = 1.95 Hz, d, J = 2.7 Hz, d, J = 1.2 Hz, C$_4$H$_3$O); 7.06 and 7.77 (2H and 2H, d and d, J = 9.0 Hz, C$_6$H$_4$OMe); 7.14 (2H, br.s, NH$_2$) |
| 44 | OSI-10280 | (DMSO-d$_6$) δ 3.72, 3.78 and 3.84 (3H, 6H and 3H, C$_6$H$_4$OMe and C$_6$H$_2$(OMe)$_3$); 6.89, 7.06 and 8.02 (2H, 2H and 2H, s, d and d, J = 9.0 Hz, C$_6$H$_2$(OMe)$_3$ and (,C$_6$H$_4$OMe); 7.70 and 7.89 (2H and 2H, br.s and br.s, 2xNH$_2$) |
| 45 | OSI-10000 | (CDCl$_3$) δ 2.51 (3H, s, 4-Me); 2.70 (3H, s, 6-Me); 3.74 and 3.80 (3H and 3H, s and s, C$_6$H$_3$(OMe)$_2$); 6.46, 6.47, 6.79, 7.33 (1H, 1H, 1H and 1H, s, s, s, d, 5-H, C$_6$H$_3$(0Me)$_2$), 7.14 (2H, s, NH$_2$) |
| 46 | OSI-10291 | (CDCl$_3$) δ 2.67 (3H, s, Me); 3.87, 3.88, and 3.93 (3H, 6H and 3H, s, s and s, C$_6$H$_4$OMe and C$_6$H$_2$(OMe)$_3$); 6.63, 6.96 and 7.87 (2H, 2H and 2H, s, d and d, J = 9.0 Hz, C$_6$H$_2$(OMe)$_3$ and C$_6$H$_4$OMe); 6.90 (2H, br.s. NH$_2$); 6.98 (1H, s, 5-H) |
| 47 | OSI-10183 | (CDCl$_3$) δ 3.91, and 3.96 (9H and 9H, s and s, 2xC$_6$H$_2$(OMe)$_3$); 6.69, 7.35, 7.44 and 7.81 (2H, 2H, 2H and 2H s, s, d, d, J = 8.6 Hz, d, J = 9.0 Hz, 2xC$_6$H$_2$(OMe)$_3$ and C$_6$H$_4$Cl); 6.95 (2H, br.s, NH$_2$); 7.50 (1H, s, 5-H) |

TABLE 5-continued

¹H NMR spectra of thieno[2,3-b]pyridines (I)

| Compound No. | Compound name | ¹H NMR spectra of compounds of formula (I) |
|---|---|---|
| 48 | OSI-10184 | (CDCl₃, δ, ppm): 3.83, 3.85, and 3.91 (3H, 9H and 9H, s, s and s, C₆H₄OMe, 2xC₆H₂(OMe)₃); 6.64 6.92, 7.30 and 7.86 (2H, 2H, 2H, s, d, J = 8.6 Hz, s, d, J = 9.0 Hz 2xC₆H₂(OMe)₃, and, C₆H₄OMe); 6.84 (2H, br.s, NH₂); 7.30 (1H, s, 5-H) |
| 49 | OSI-10272 | (CDCl₃) δ 1.51 (3H, s, COMe); 2.73 (3H, s, Me); 3.28, 3.36 and 4.20 (3H, 2H and 2H, s, t and t, J = 4.7 Hz, COO(CH₂)₂OMe); 3.87 3.88 and 3.90 (6H, 3H and 3H, s, s and s, C₆H₂(OMe)₃ and C₆H₄OMe); 6.60, 6.94 and 7.94 (2H, 2H and 2H, s, d and d, J = 8.6 Hz, C₆H₂(OMe)₃ and C₆H₄OMe); 7.19 (1H, s, NH) |

TABLE 6

Synthesized 1,6-dihydro-6-thioxopyridines II-1 as intermediates of MDR modulators I.

| Compound No. | R¹ | R² | R⁶ | Yield of II, % Path A | Yield of II, % Path B | Mp, °C. |
|---|---|---|---|---|---|---|
| 50 | Me | COMe | 3,4-(OMe)₂ | 47 | | 234-235 |
| 51 | Me | COMe | 3,4,5-(OMe)₃ | 42 | | 244-246 |
| 52 | Me | COOMe | 3,4-(OMe)₂ | 42 | | 230-232 |
| 53 | Me | COOMe | 3,4,5-(OMe)₃ | 29 | 33 | 233-234 |
| 54 | Me | COOEt | 3-OMe | | 61 | 220-221 |
| 55 | Me | COOEt | 3-OMe, 4-OH | 29 | | 206-208 |
| 56 | Me | COOEt | 4-OEt | | 54 | 184-185 |
| 57 | Me | COOEt | 4-OBu(n) | | 59 | 175-176 |
| 58 | Me | COOBu(n) | 3,4,5-(OMe)₃ | | 46 | 197-198 |
| 59 | Me | COOC₂H₄OMe | 4-OMe | | 53 | 210-211 |
| 60 | Me | COOC₂H₄OMe | 3,4,5-(OMe)₃ | 42 | 53 | 192-194 |
| 61 | Me | COOC₂H₄OPr | 3,4,5-(OMe)₃ | 57 | | 140-141 |
| 62 | 3,4,5-(OMe)₃C₆H₂ | COOEt | 3,4,5-(OMe)₃ | | 44 | 215-216 |
| 63 | NH₂ | CN | 3,4,5-(OMe)₃ | | 41 | 252-253 |

TABLE 7

¹H NMR spectra of compounds of formula (II-1)

| Compound No. | ¹H NMR spectra of 1,6-dihydro-6-thioxopyridines (II-1) |
|---|---|
| 50 | (CDCl₃) δ 1.80 (3H, s, COMe); 2.50 (3H, s, Me); 3.90 and 3.95 (3H and 3H, s and s, C₆H₃(OMe)₂); 6.92-7.00 (3H, m, C₆H₃(OMe)₂); 12.53 (1H, br.s, NH) |
| 51 | (CDCl₃) δ 1.83 (3H, s, COMe); 2.50 (3H, s, Me); 3.87 and 3.92 (3H and 6H, s and s, C₆H₂(OMe)₃); 6.62 (2H, C₆H₂(OMe)₃); 12.16 (1H, br.s, NH) |
| 52 | (CDCl₃) δ 2.58 (3H, s, Me); 3.54 (3H, s, COOMe); 3.90 and 3.93 (3H and 3H, s and s, C₆H₃(OMe)₂); 6.90-6.98 (3H, m, C₆H₃(OMe)₂); 12.50 (1H, br.s, NH) |
| 53 | (CDCl₃) δ 2.58 (3H, s, Me); 3.54 (3H, s, COOMe); 3.87 and 3.90 (6H and 3H, s and s, C₆H₂(OMe)₃); 6.60 (2H, s, C₆H₂(OMe)₃ |
| 54 | (CDCl₃) δ 0.87 and 3.96 (3H and 2H, t and q, J = 7.0 Hz, COOEt); 2.60 (3H, s, Me); 3.83 (3H, s, C₆H₄OMe); 6.88-7.40 (4H, m, C₆H₄OMe); 12.39 (1H, br.s, NH) |
| 55 | (CDCl₃) δ 0.81 and 3.90 (5H, t and q, J = 7.0, COOEt); 2.40 (3H, s, Me); 3.72 (3H, s, C₆H₃OMe); 6.73-6.89 (3H, m, C₆H₃OMe), 9.57 (1H, s, OH), 14.21 (1H, s, NH) |
| 56 | (CDCl₃) δ 0.91 and 3.98 (3H and 2H, t and q, J = 7.0 Hz, C₆H₄OEt); 1.44 and 4.07 (3H and 2H, t and q, J = 7.0 Hz, COOEt); 2.57 (3H, s, Me); 6.97 and 7.31 (2H and 2H, d and d, J = 8.6 Hz, C₆H₄OEt ); 12.06 (1H br.s, NH) |

TABLE 7-continued

¹H NMR spectra of compounds of formula (II-1)

| Compound No. | ¹H NMR spectra of 1,6-dihydro-6-thioxopyridines (II-1) |
|---|---|
| 57 | (CDCl₃) δ 0.92, 0.99, 1.50, 1.79 and 3.97-4.02 (3H, 3H, 2H, 2H and 4H, t, se, J = 7.0 Hz, qui, t, J = 6.3 Hz, m, C₆H₄OBu and COOEt); 2.58 (3H, s, Me); 6.96 and 7.31 (2H and 2H, d and d, J = 9.0 Hz, C₆H₄OBu); 12.41 (1H, br.s, NH) |
| 58 | (CDCl₃) δ 0.79, 1.05, 1.25 and 3.92 (3H, 2H, 2H and 2H, t, se, J = 7.0 Hz, qui and t, J = 6.3 Hz, COOBu); 2.59 (3H, s, Me); 3.87 and 3.90 (3H and 6H, s and s, C₆H₂(OMe)₃); 6.61 (2H, s, C₆H₂(OMe)₃) ); 12.40 (1H, br.s, NH) |
| 59 | (CDCl₃) δ 2.57 (3H, s, Me); 3.24-3.28 and 4.09 (5H and 2H, m and t, J = 4.7 Hz, COO(CH₂)₂OMe); 3.86 (3H, s, C₆H₄OMe); 6.99 and 7.34 (2H and 2H, d and d, J = 8.6 Hz, C₆H₄OMe) |
| 60 | (CDCl₃) δ 2.58 (3H, s, Me); 3.21-3.23 and 4.07 (5H and 2H, m and t, J = 4.7 Hz, COO(CH₂)₂OMe); 3.86 and 3.89 (6H and 3H, s and s, C₆H₂(OMe)₃); 6.59 (2H, s, C₆H₂(OMe)₃); 12.57 (1H, s, NH) |
| 61 | (CDCl₃) δ 0.87, 1.5, 3.25-3.30, 4.10 (3H, 2H, 4H, 2H t, se, J = 7 Hz m, t, J = 4.7 Hz, COO(CH₂)₂OPr); 2.17 (3H, s, Me); 3.87 and 3.90 (6H and 3H, s and s, C₆H₂(OMe)₃); 6.61 (2H, s, C₆H₂(OMe)₃); 12.71 (1H, br.s, NH) |
| 62 | (CDCl₃) δ 0.87 and 4.00 and (3H and 2H, t and q, J = 7.0 Hz, COOEt); 3.86 and 3.90 (9H and 9H, s and s, 2xC₆H₂(OMe)₃); 6.57 and 6.88 (2H and 2H, s and s, 2xC₆H₂(OMe)₃); 8.67 (1H, s, NH) |
| 63 | (CDCl₃) δ 3.71 and 3.77 (6H and 3H, s and s, C₆H₂(OMe)₃); 6.84 (2H, s and s, C₆H₂(OMe)₃); 7.96 (2H, br.s, NH₂); 8.86 (1H, s, NH) |

Preparation of the Intermediates—1,6-dihydro-6-thioxopyridines with General Formula (II-1). Path A been prepared. The yields and melting points are combined in table 6, but ¹H NMR (400 MHz) spectra in table 7.

Preparation of the Intermediates—α,β-unsaturated Ketones 64-66

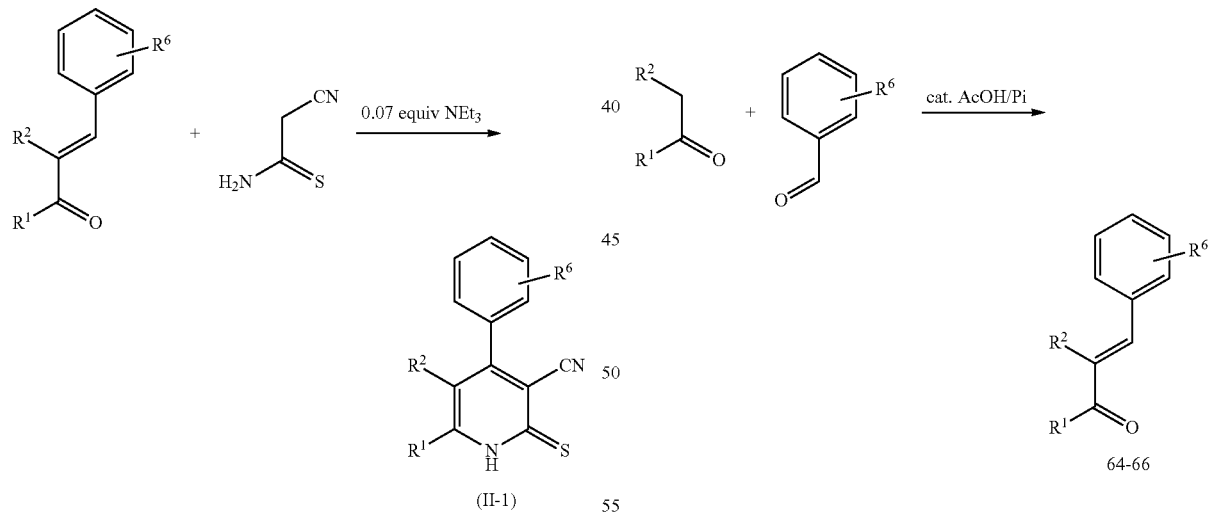

A mixture of 3-(4,5-dimethoxybenzylidene)pentane-2,4-dione (1.24 g, 5 mmol), 2-cyanothioacetamide (0.50 g, 5 mmol) and triethylamine (0.05 ml, 0.35 mmol) in 20 ml of ethanol was refluxed for 15 h. The precipitated crystals were separated by filtration and purified by washing with ethanol and water during the filtration to give 0.77 g (47%) of 5-acetyl-4-(3,4-dimethoxyphenyl)-6-methyl-2-thioxo-1,2-dihydropyridine-3-carbonitrile (50) (general formula (II-1)) as yellow powder. In a similar manner 6-thioxo-1,6-dihydropyridines 51-53, 55, 60, 61 (general formula (II-1)) have To a solution of 3-oxo-butyric acid 2-methoxy ethyl ester (8.00 g, 50 mmol) of and 3,4,5-trimethoxybenzaldehyde (9.81 g, 50 mmol) in 50 ml of 2-propanol, piperidine (0.35 ml, 3.5 mmol) and acetic acid (1.55 ml, 27 mmol) were added and reaction mixture was refluxed for one day. After solvent was evaporated, DCM was added and the reaction mixture was washed with NaHCO₃ aqueous solution. The organic layer was dried over anhydrous MgSO₄ and then concentrated under reduced pressure to give 14.21 g (84%) of E,Z-3-oxo-2-[1-(3,4,5-trimethoxyphenyl)methylidene] butyric acid 2-methoxy ethyl ester (66) as colourless powder with mp 92-93° C. ¹H NMR (CDCl₃) δ 2.38 and 2.42 (0.5H and 2.5H, s and s, Me); 3.31 and 3.40, 3.62 and 3.70, 4.39 and 4.43 (2.5H and 0.5H, 1.7H and 0.3H, 0.3H and 1.7H, s and s, t and t, t and t, J=4.7 Hz, COO(CH$_2$)$_2$OMe); 3.84-3.89 (9H, m, C$_6$H$_2$(OMe)$_3$); 6.66 and 6.74 (0.3H and 1.7H, s and s, C$_6$H$_2$(OMe)$_3$); 7.49 and 7.61 (0.9H and 0.1H, s and s, 3-H).

In a similar manner α,β-unsaturated ketones 65 and 66 have been prepared.

3-Oxo-2-[1-(3,4,5-trimethoxyphenyl)-methylidene] butyric acid 2-propoxy ethyl ester (65)

Yield 89%, mp 81-82° C. $^1$H NMR (CDCl$_3$) δ 2.42 (3H, s, Me); 0.84, 1.52, 3.35, 3.66 and 4.42 (3H, 2H, 2H, 2H and 2H, t, J=7.4 Hz, se, J=7.0 Hz, t, J=6.7 Hz, t, J=5.1 Hz, and t, J=5.1 Hz, COO(CH$_2$)$_2$OPr(n)); 3.86 and 3.89 (6H and 3H, s and s, C$_6$H$_2$(OMe)$_3$); 6.74 (2H, s and s, C$_6$H$_2$(OMe)$_3$); 7.49 (1H, s and s, 3-H).

2-(3,4,5-Trimethoxybenzoyl)-3-(3,4,5-trimethoxyphenyl)acrylic acid ethyl ester (66)

Yield 86%, mp 101-103° C. $^1$H NMR (CDCl$_3$) δ 1.24 and 4.26 (3H and 2H, t and q, J=7.0 Hz, COOEt); 3.66, 3.81, 3.83 and 3.91 (6H, 3H, 6H and 3H, s, s, s and s, 2×C$_6$H$_2$(OMe)$_3$); 6.65 and 6.96 (2H and 2H, s and s, 2×C$_6$H$_2$(OMe)$_3$); 7.85 (1H, s, 3-H).

Preparation of the Intermediates—1,6-dihydro-6-thioxopyridines with General Formula (II-1). Path B

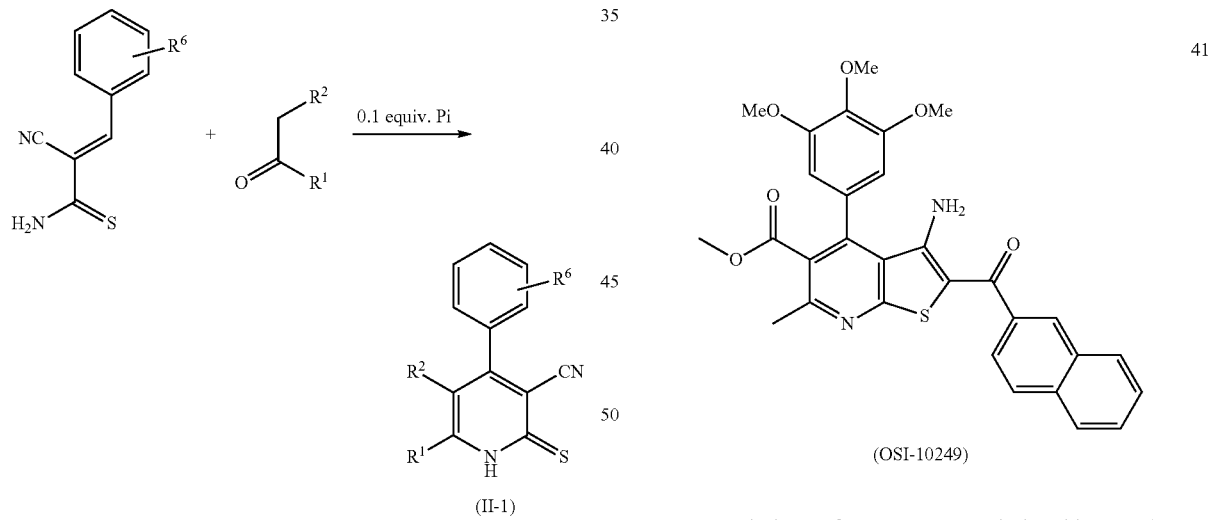

A mixture of 2-cyano-3-(4-ethoxyphenyl)thioacrylamide (1.16 g, 5 mmol), ethyl acetoacetate (0.637 ml, 5 mmol) and piperidine (0.05 ml, 0.5 mmol) in 25 ml of ethanol was refluxed for 15 h. The precipitated crystals were separated by filtration and purified by washing with ethanol and water during the filtration to give 1.04 g (61%) of 5-cyano-4-(4-ethoxyphenyl)-2-methyl-6-thioxo-1,6-dihydropyridine-3-carboxylic acid ethyl ester 54.

In a similar manner 6-thioxo-1,6-dihydropyridines 53, 56-60 and 62 (general formula (II-1)) have been prepared. The yields and melting points are combined in table 6, but $^1$H NMR (400 MHz) spectra in table 7.

Preparation of thieno[2,3-b]pyridines (I-2) from Intermediates (II) (Examples 1-5)

$^1$H NMR (400 MHz) spectra of thieno[2,3-b]pyridines 41-45 (general formula (I-2)) are combined in table 5.

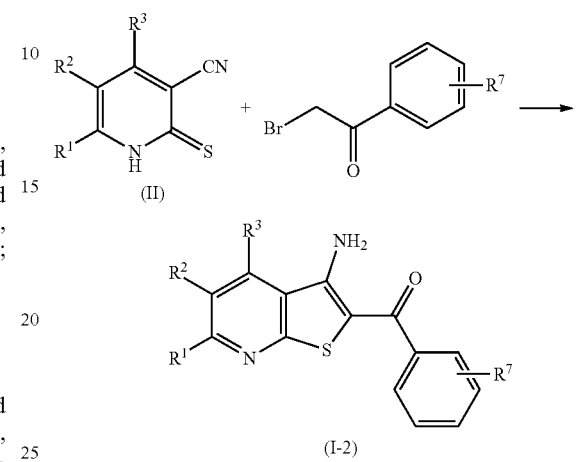

Reagents and conditions:
1) 2.4 equiv 3M NaOH/H$_2$O, rt, 10 min, EtOH;
2) 2-bromoacethophenone, 78° C., 2-3 min, then rt, 30 min

Example 1

41

(OSI-10249)

To a solution of 5-cyano-2-methyl-6-thioxo-4-(3,4,5-trimethoxyphenyl)-1,6-dihydropyridine-3-carboxylic acid methyl ester (53) (0.69 g, 2 mmol) in 10 ml of ethanol 3M sodium hydroxide water solution (1.60 ml, 4.8 mmol) was added and stirred at room temperature for 10 min. Then 2-bromo-1-naphthalen-2-yl-ethanone (0.50 g, 2 mmol) was added and reaction mixture was shortly refluxed (0.5 min) and stirred for 30 min at room temperature. The precipitate was filtered and purified by washing with 3 ml of cold methanol and water during the filtration to give 0.97 g (89%) of 3-amino-6-methyl-2-(naphthalene-2-carbonyl)-4-(3,4,5-trimethoxyphenyl)thieno[2,3-b]pyridine-5-carboxylic acid methyl ester (41) as yellow powder with mp 150-151° C.

Example 2

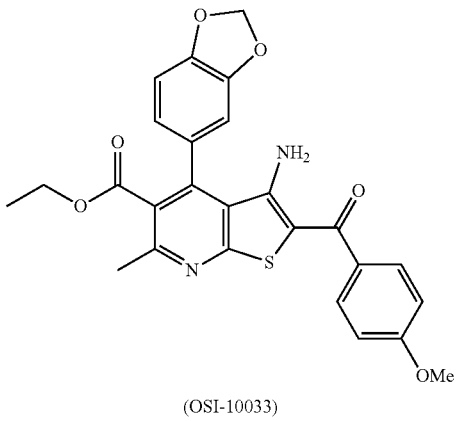

(OSI-10033)

To a solution of 4-(benzo[1,3]dioxol-5-yl)-5-cyano-2-methyl-6-thioxo-1,6-dihydropyridine-3-carboxylic acid ethyl ester (in Abunada et al., Phosphorus, Sulfur Silicon Rel Elem 3: 591-601 (2009)) (0.17 g, 0.5 mmol) in 5 ml of ethanol 3M sodium hydroxide water solution (0.4 ml, 1.2 mmol) was added and stirred at room temperature for 10 min. Then 2-bromo-4'-methoxyacetophenone (0.11 g, 0.5 mmol) was added and reaction mixture was shortly refluxed and stirred at room temperature for 30 min. The precipitated crystals were separated by filtration and purified by washing with ethanol and water during the filtration to give 0.19 g (79%) of 3-amino-4-(benzo[1,3]dioxol-5-yl)-2-(4-methoxybenzoyl)-6-methylthieno[2,3-b]pyridine-5-carboxylic acid ethyl ester (42) as yellow powder with mp 168-170° C.

Example 3

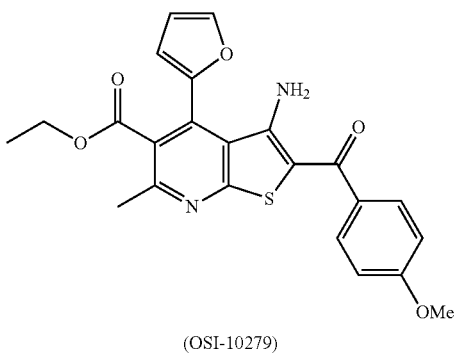

(OSI-10279)

To a solution of 5-cyano-4-(furan-2-yl)-2-methyl-6-thioxo-1,6-dihydropyridine-3-carboxylic acid ethyl ester (in Elgemeie et al., Bull Chem Soc Jpn 12: 4431-34 (1988)) (0.30 g, 1 mmol) in 10 ml of ethanol 3M sodium hydroxide water solution (0.8 ml, 2.4 mmol) was added and stirred at room temperature for 10 min. Then 2-bromo-4'-methoxyacetophenone (0.24 g, 1 mmol) was added and reaction mixture was shortly refluxed and stirred at room temperature for 30 min. The precipitated crystals were separated by filtration and purified by washing with ethanol and water during the filtration to give 0.40 g (88%) 3-amino-4-(furan-2-yl)-2-(4-methoxybenzoyl)-6-methylthieno[2,3-b]pyridine-5-carboxylic acid ethyl ester (43) as yellow powder with mp 113-114° C.

Example 4

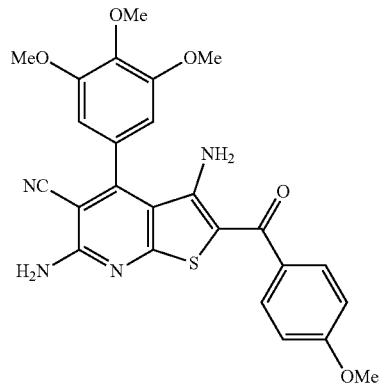

(OSI-10280)

To a solution of 6-amino-2-thioxo-4-(3,4,5-trimethoxyphenyl)-1,2-dihydropyridine-3,5-dicarbonitrile (63) (0.34 g, 1 mmol) in 10 ml of ethanol 3M sodium hydroxyde water solution (0.8 ml, 2.4 mmol) was added and stirred at room temperature for 10 min. Then 2-bromo-4'-methoxyacetophenone (0.24 g, 1 mmol) was added and reaction mixture was shortly refluxed and stirred at room temperature for 30 min. The precipitated crystals were separated by filtration and purified by washing with ethanol and water during the filtration to give 0.20 g (41%) of 3,6-diamino-2-(4-methoxybenzoyl)-4-(3,4,5-trimethoxyphenyl)thieno[2,3-b]pyridine-5-carbonitrile (44) as yellow powder with mp 241-242° C.

Example 5

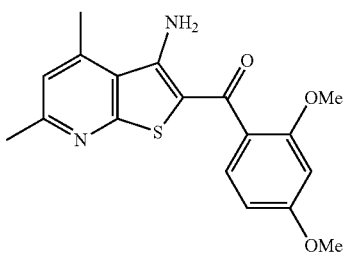

(OSI-10000)

To a solution of 4,6-dimethyl-2-thioxo-1,2-dihydropyridine-3-carbonitrile (in Schmidt, Kubitzek, Chemische Berichte 93: 1559-1565 (1960)) (0.16 g, 1 mmol) in 10 ml of ethanol 3M sodium hydroxyde water solution (0.8 ml, 2.4 mmol) was added and stirred at room temperature for 10 min. Then 2-bromo-4'-methoxyacetophenone (0.24 g, 1 mmol) was added and reaction mixture was shortly refluxed and stirred at room temperature for 30 min. The precipitated crystals were separated by filtration and purified by washing with ethanol and water during the filtration to give 0.24 g (70%) 3-amino-4,6-dimethyl-2-(2,4-dimetoxybenzoyl)thieno[2,3-b]pyridine (45) as yellow powder with mp 184-186° C.

Preparation of thieno[2,3-b]pyridines 46-49
(General Formula (I)) (Examples 6-9)

$^1$H NMR (400 MHz) spectra of compounds 46-49 (general formula (I)) are combined in table 5.

Example 6

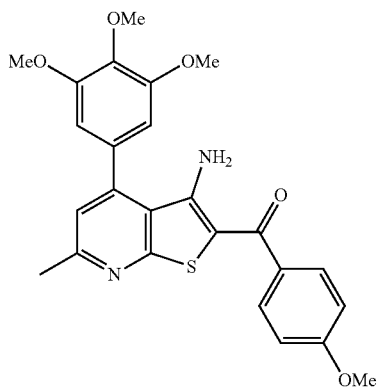

46

(OSI-10291)

A mixture of 4-(3,4,5-trimethoxyphenyl)-3-buten-2-one (0.24 g, 1 mmol), 2-cyanothioacetamide (0.1 g, 1 mmol) and piperidine (0.11 ml, 1.1 mmol) in 10 ml of ethyl alcohol was stirred at room temperature for 12 h. Then 2-bromo-1-(4-methoxyphenyl)ethanone (0.23 g, 1 mmol) was added and reaction mixture was shortly heated until reflux and stirred for 3 h at room temperature. Then 3M sodium hydroxide water solution (0.33 ml, 1 mmol) was added. Reaction mixture was refluxed for 1 min and stirred at room temperature for 30 min. The precipitates was filtered and purified by washing with 1 ml of cold ethanol and water during the filtration to give 0.39 g (84%) of 3-amino-2-(4-methoxybenzoyl)-6-methyl-4-(3,4,5-trimethoxyphenyl) thieno[2,3-b]pyridine (46) as yellow powder with mp 234-235° C.

Example 7

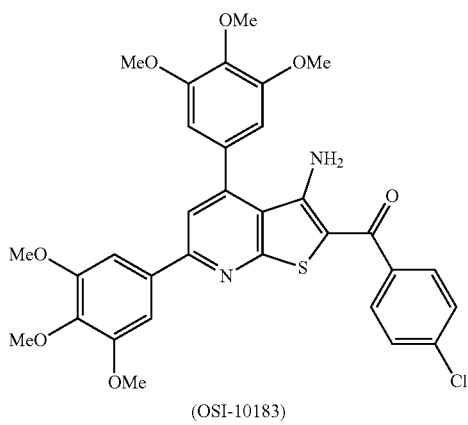

47

(OSI-10183)

In a similar manner 3-amino-4,6-bis-(3,4,5-trimethoxyphenyl)-2-(4-chlorobenzoyl)thieno[2,3-b]pyridine (47) has been prepared. Yield 88%, mp 259-260° C.

Example 8

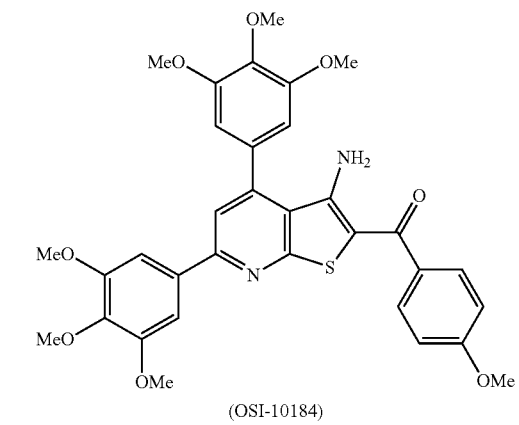

48

(OSI-10184)

In a similar manner 3-amino-4,6-bis-(3,4,5-trimethoxyphenyl)-2-(4-methoxybenzoyl)-thieno[2,3-b]pyridine (48) has been prepared. Yield 84%, mp 243-244° C.

Example 9

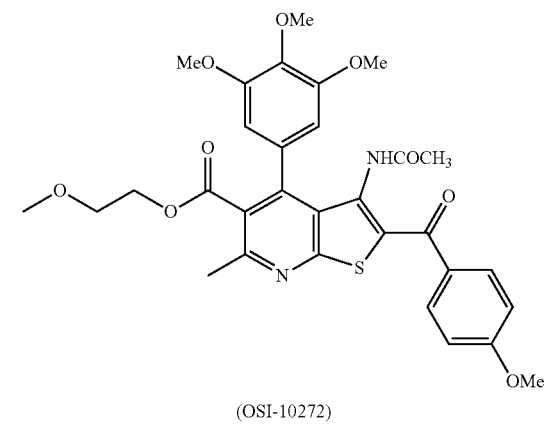

49

(OSI-10272)

To solution of 3-amino-2-(4-methoxybenzoyl)-6-methyl-4-(3,4,5-trimethoxyphenyl)thieno[2,3-b]pyridine-5-carboxylic acid 2-methoxyethyl ester (34) (OSI-10205) (0.19 g, 0.35 mmol) in 2.5 ml acetyl chloride NaOH (0.014 g, 0.35 mmol) were added. The resulting mixture was refluxed for 2 h, cooled down, poured into iced water, neutralized with NaHCO$_3$ and extracted with DCM. Resulting extract was dried over MgSO$_4$ and evaporated. Oil was recrystallized using EtOH. The precipitated crystals were separated by filtration and purified by washing with ethanol and water during the filtration to give 0.15 g (71%) of 3-acetylamino-2-(4-methoxybenzoyl)-6-methyl-4-(3,4,5-trimethoxyphenyl)-thieno[2,3-b]pyridine-5-carboxylic acid 2-methoxyethyl ester (49) as yellow powder with mp 183-184° C.

Biological Studies of thieno[2,3-b]pyridines

The potency of P-glycoprotein-mediated MDR modulator in vitro was evaluated in the drug sensitive human sarcoma MES-SA cells and doxorubicin (DOX) resistant cells by accumulation of fluorescent substrate—rhodamine 123. Effects on MRP1-mediated drug efflux were observed in the DOX resistant human lung carcinoma H69AR cells using calcein AM assay. BCRP1-mediated drug efflux was also evaluated using fluorescent substrate Hoechst 33342 in the mitoxantrone resistant human sarcoma MESSA/MX2 cells. The half maximal effective concentrations ($EC_{50}$) were calculated from dose response curve as the most effective method to compare MDR-modulating activities of compounds. MDR modulating activity, intracellular $Ca^{2+}$ values and $LD_{50}$ values of tested compounds of formula (I) are given in table 3.

Measurement of P-Glycoprotein Activity

About 50,000 cells/well of the human uterine sarcoma cell line MESSA and MES-SA/Dx5 were seeded into the 96-well plates and incubated for 24 h. The MDR modulators were incubated with the cells for 15 min. Then rhodamine-123 (2.6 μM) was added and the cells were incubated for 1 h, 37° C., 5% $CO_2$. The cells were washed twice with phosphate buffered saline (PBS) and fluorescence values were measured with excitation at 487 nm and emission at 557 nm by using the fluorescence reader Tecan infinite M1000. Verapamil, the known P-glycoprotein inhibitor was used as a positive control. The $EC_{50}$ values were calculated using the program Graph Pad Prism® 4.0.

Measurement of MRP1 Activity

About 60,000 cells/well of the human lung carcinoma cell line H69 and H69AR were seeded into the 96-well plates and incubated for 24 h. The compounds were incubated with the cells for 15 min. Then Calcein AM (0.25 μM) was added and the cells were incubated for 30 min, 37° C., 5% $CO_2$. The cells were washed twice with phosphate buffered saline (PBS) and fluorescence values were measured with excitation at 494 nm and emission at 517 nm by using the fluorescence reader Tecan infinite M1000. MK-571 was used as the known inhibitor of MRP1. The $EC_{50}$ values was calculated using the program Graph Pad Prism® 4.0

Measurement of BCRP Activity

About 50,000 cells/well of the MESSA and MES-SA/MX2 were seeded into the 96-well plates and incubated for 24 h. The MDR modulators were incubated with the cells for 15 min. Hoechst 33342 (5 μg/ml) was added and the cells were incubated for 90 min, 37° C., 5% $CO_2$. The cells were washed twice with phosphate buffered saline (PBS) and fluorescence values were measured with excitation at 360 nm and emission at 450 nm (Gail M. Seigel and Lorrie M. Campbell, 2004). Imatinib was used as a positive control. The $EC_{50}$ values were calculated using the program Graph Pad Prism® 4.0

Intracellular $Ca^{2+}$ Measurements

Many calcium channel blockers of all subclasses (phenylalkylamine, dihydropyridine and benzothiazepine type) and other calcium antagonists inhibit the P-gp-mediated drug efflux. Calcium antagonists are overcoming P-gp-mediated MDR by mechanisms distinct from their inhibitory effect on voltage-dependent calcium channels. These mechanisms include not only direct interactions with the P-gp protein but also interactions with several other proteins that may indirectly alter P-gp transport activity. Calcium antagonists not only can be inhibitors of P-gp but at the same time some may inhibit P-gp expression via P-gp mRNA down-regulation. The clinical application of calcium antagonists is limited by their severe cardiovascular side effects associated with the high concentration required for reversal of MDR. Hence, cardiotoxicity is a major complication of anticancer drugs including anthracyclines and 5-fluorouracils.

The effective MDR modulators with the less than ten times lower $Ca^{2+}$ antagonist effect than verapamil, the known P-gp inhibitor, allow to decrease presumable cardiovascular side effects.

Changes in intracellular $[Ca^{2+}]i$ concentration were studied using Fluo-4 NW Calcium Assay Kit ("Invitrogen", Sweden) accordingly to manufacturer's instructions. The A7R5 (rat aorta smooth muscle) cells were grown at 37° C. in a humidified atmosphere with 5% $CO_2$/95% air in DMEM medium containing 2 mM glutamine and supplemented with 10% FBS. The cells were seeded into 96 well plate at 10,000 cells/well and incubated for 72 h. The cells were loaded with Fura-4NW for 45 min. The Fura-4NW loaded cells were pre-incubated in the dark for 15 minutes with tested compounds at concentrations from 0.8 to 100 μM. Then A7R5 cells were pre-treated with 1.5 mM $CaCl_2$ for 5 minutes and KCl (50 mM) was added to A7R5 cells to induce $[Ca^{2+}]i$ increase. Amlodipine, the well-known calcium channel inhibitor was used as the positive control. Changes in $[Ca^{2+}]i$ were measured from the fluorescence emitted at 516 nm due to alternate excitation at 494 nm using the fluorescence spectrophotometer (Thermo Ascient, Finland). The $IC_{50}$ values were calculated using the program Graph Pad Prism® 4.0

Basal Toxicity Test

A low therapeutic index of chemotherapy agents is due to affecting not only cancer formation but also normal cells. Compounds (I) were tested on NIH 3T3 (normal mouse fibroblasts, "ATCC") cell line according the basal toxicity test (INVITOX Protocol No 64, 1992) and non-toxic compounds were selected.

9,000 NIH 3T3 cells/well were placed into 96-well plates for 24 h and then exposed to the test compound over a range of eight concentration (1-1000 μg/ml) for 24 h. Upon that, the cells were incubated with the neutral red dye for 4 h and then OD was determined at 540 nm. Alternative $LD_{50}$ values ($LD_{50}$ value is the amount of the drug that is taken to kill 50% of the test animals) was calculated according to the formula: $\log (LD_{50} [mmol/kg]=0.435 \times \log (IC_{50} [mmol/l])= 0.625$. The $IC_{50}$ values were calculated using the program Graph Pad Prism® 4.0

Cell Culture

NIH3T3 (normal mouse fibroblasts), HT-1080 (human fibrosarcoma), MG-22A (mouse hepatoma), MES-SA (human uterine sarcoma), MES-SA/Dx5 (Doxorubicin resistant, 300 ng/ml), H69 (human lung carcinoma), H69/AR (Doxorubicin resistant) and A7R5 (rat aorta smooth muscle) cells were obtained from the ATCC cell collection.

MDR appearance is the process of activation of a number of gens and as a result of several proteins overexpression (48 human ABC transporters have been described, more probable MDR associated proteins are P-pg, MRP1 and BCRP).

The invention claimed is:
1. The compound comprising 3-Amino-2-(4-methoxybenzoyl)-6-methyl-4-(3,4,5-trimethoxyphenyl)thieno[2,3-b]-pyridine-5-carboxylic acid 2-methoxyethyl ester, or pharmaceutically acceptable salts, hydrates, solvates and polymorphs thereof.

2. A compound of the formula:
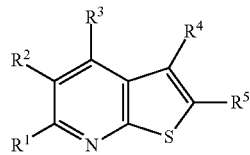
wherein:
  $R^1$=Me;
  $R^2$=COOC$_2$H$_4$OMe;
  $R^3$=3,4,5-trimethoxyphenyl;
  $R^4$=NH$_2$; and
  $R^5$=COC$_6$H$_4$-(4-OMe).
3. A compound of the formula:
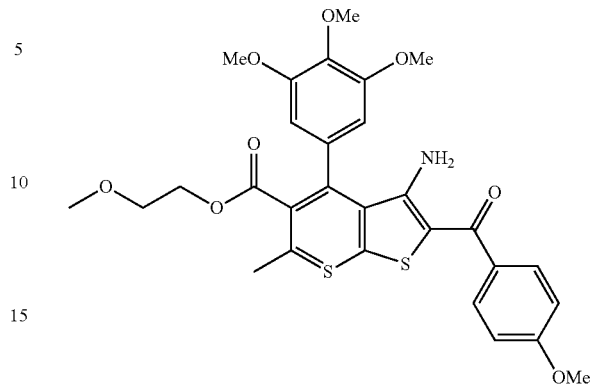
or pharmaceutically acceptable salts, hydrates, solvates and polymorphs thereof.
4. A composition a compound of claim 1, 2, or 3 and one or more pharmaceutically acceptable excipients or vehicles.
* * * * *